US012337973B2

(12) United States Patent
Tillack et al.

(10) Patent No.: US 12,337,973 B2
(45) Date of Patent: Jun. 24, 2025

(54) METHODS, SYSTEMS, AND APPARATUSES FOR REDUCING OZONE CONCENTRATION AND REDUCING VOC CONCENTRATION IN AIRCRAFT CABIN ENVIRONMENT RECIRCULATED AIRFLOW

(71) Applicant: The Boeing Company, Chicago, IL (US)

(72) Inventors: Bryce A. Tillack, Everett, WA (US); Stephen M. Trent, Seattle, WA (US); Kevin J. Kelly, Mukilteo, WA (US); Brian C. Christenson, Arlington, WA (US)

(73) Assignee: THE BOEING COMPANY, Arlington, VA (US)

( * ) Notice: Subject to any disclaimer, the term of this patent is extended or adjusted under 35 U.S.C. 154(b) by 808 days.

(21) Appl. No.: 17/577,221

(22) Filed: Jan. 17, 2022

(65) Prior Publication Data

US 2023/0227165 A1    Jul. 20, 2023

(51) Int. Cl.
*B64D 13/06*     (2006.01)
*A61L 9/00*      (2006.01)

(52) U.S. Cl.
CPC ............... *B64D 13/06* (2013.01); *A61L 9/00* (2013.01); *A61L 2209/21* (2013.01); *B64D 2013/064* (2013.01); *B64D 2013/0685* (2013.01); *B64D 2013/0688* (2013.01)

(58) Field of Classification Search
CPC ...... B64D 2013/0625; B64D 2013/064; B64D 2013/0655; B64D 2013/0685; B64D 2013/0688; B64D 13/00; B64D 13/06; F24F 2110/66; F24F 2110/74; F24F 8/98; F24F 8/167; B01D 53/8675; B01D 53/88; B01D 2259/4575; B01D 2257/106; B01D 2257/708

See application file for complete search history.

(56) References Cited

U.S. PATENT DOCUMENTS

| | | | | |
|---|---|---|---|---|
| 5,516,330 | A | * | 5/1996 | Dechow ................ B64D 13/08 165/235 |
| 2009/0227195 | A1 | * | 9/2009 | Buelow .............. B01J 20/28064 454/76 |
| 2022/0177141 | A1 | * | 6/2022 | Shea ...................... B64D 13/06 |

OTHER PUBLICATIONS

Bagshaw et al., "The Aircraft Cabin Environment", Travel Medicine, Nov. 26, 2018, pp. 429-436 (Year: 2018).*
Federal Aviation Administration, Advisory Circular: "Flightdeck Protection (Smoke and Fumes)", Oct. 24, 2008 (Year: 2008).*

* cited by examiner

*Primary Examiner* — Jennifer Wecker
*Assistant Examiner* — Brady C Pilsbury
(74) *Attorney, Agent, or Firm* — COATS & BENNETT, PLLC

(57) ABSTRACT

Ozone converters containing differing ozone converting materials are provided into air aircraft airflow management systems, with the ozone converter positioned in an air management architecture at positions configured to assist replacement, and maintenance, and with the ozone converters further positioned downstream of air conditioning packs, and with the ozone converters configured to reduce at least one of ozone concentrations and volatile organic compound concentrations from airflows directed to passenger cabin air volumes and flight deck air volumes.

9 Claims, 10 Drawing Sheets

METHODS, SYSTEMS, AND APPARATUSES FOR REDUCING OZONE CONCENTRATION AND REDUCING VOC CONCENTRATION IN AIRCRAFT CABIN ENVIRONMENT RECIRCULATED AIRFLOW

TECHNOLOGICAL FIELD

The present disclosure relates generally to the field of air treatment and air purification. More specifically, the present disclosure relates to the field of air treatment and air purification including ozone concentration reduction and volatile organic compound concentration reduction from an airflow delivered to an enclosed environment including, for example, aircraft cabins.

BACKGROUND

Air management systems for enclosed environments can include air filtering and air conditioning apparatuses and systems designed to filter and condition circulated air. In aircraft, such air management systems are responsible for treatment of air that is directed into aircraft compartments including, for example, passenger cabins. One air component of concern that is typically present in a passenger compartment is ozone ($O_3$). During flight, ozone concentration, if left untreated, can rise to concentrations in an air supply that can be irritating to passengers.

Unless explicitly identified as such, no statement herein is admitted as prior art merely by its inclusion in the Technological Field and/or Background section.

SUMMARY

Present aspects are disclosed that are directed to the treatment of air in aircraft compartments that can include, for example, aircraft passenger cabins and flight decks. Further present aspects are directed to methods, apparatuses, and systems, including air management systems for reducing ozone concentration and volatile organic compounds (VOCs) from a conditioned air supply for a passenger compartment that can include, for example, an aircraft passenger compartment and a flight deck. Presently disclosed methods, systems and apparatuses herein will facilitate at least one of an enhanced ozone concentration reduction from an aircraft cabin environment airflow and an enhanced VOC concentration reduction from an aircraft cabin environment airflow. Accordingly, the presently disclosed terms "ozone and/or VOC converter" means that the converter can convert and reduce the concentration in an airflow of at least one of ozone and VOCs. The term "ozone and/or VOC catalyst", means at least one of an ozone catalyst and a VOC catalyst. The term "ozone and/or VOC reducing material" means at least one of an ozone reducing material and a VOC reducing material.

A present aspect is directed to an air purification system, with the air purification system including at least one air conditioning pack, and a first airflow sub-circuit configured to deliver a first conditioned airflow to a passenger cabin air volume, with the first conditioned airflow in communication with the at least one air conditioning pack. The first airflow sub-circuit further includes at least one first airflow sub-circuit first ozone converter, with the least one first airflow sub-circuit first ozone converter including a first ozone reducing material, and with the at least one first airflow sub-circuit first ozone converter located upstream of or coincident with the at least one air conditioning pack. The first airflow sub-circuit further includes at least one first airflow sub-circuit second ozone converter, with the least one first airflow sub-circuit second ozone converter including at least one of a second ozone reducing material and a VOC reducing material and with the at least one first airflow sub-circuit second ozone converter located downstream of the at least one air conditioning pack. The air purification system further includes a second airflow sub-circuit configured to deliver a second conditioned airflow to a flight deck air volume, with the second airflow sub-circuit configured to exclude entry of conditioned air from the first airflow sub-circuit into the second airflow sub-circuit. The second airflow sub-circuit includes at least one second airflow sub-circuit ozone converter with the at least one second airflow sub-circuit ozone converter including the at least one of the second ozone reducing material and the VOC reducing material, and with the at least one second airflow sub-circuit ozone converter located downstream of the at least one air conditioning pack.

In another aspect the air purification circuit further includes a mix manifold located downstream of and in communication with the at least one air conditioning pack.

In another aspect, the at least one first airflow sub-circuit further includes at least one passenger cabin airflow inlet, with the at least one passenger cabin airflow inlet located downstream of the mix manifold, and with at least one recirculation fan in communication with the mix manifold.

In a further aspect, the at least one first airflow sub-circuit further includes a plurality of passenger cabin airflow inlets, with the plurality of passenger cabin airflow inlets located downstream of the mix manifold.

In another aspect, the air purification system, further includes an auxiliary airflow sub-circuit, with the auxiliary airflow sub-circuit including at least one auxiliary recirculation fan configured to direct an auxiliary airflow, with the auxiliary airflow in communication with at least one passenger cabin auxiliary inlet, and with the auxiliary airflow sub-circuit not in ducted communication with the mix manifold.

In another aspect, the at least one second airflow sub-circuit further comprises at least one flight deck cabin airflow inlet, with the at least one flight deck cabin airflow inlet in communication with the at least one second airflow sub-circuit second ozone converter.

In another aspect, the first ozone reducing material differs from the at least one of the second ozone reducing material and the VOC reducing material.

In another aspect, the first airflow sub-circuit includes a plurality of first airflow sub-circuit second ozone converters, with the plurality of first airflow sub-circuit second ozone converters located proximate to and downstream of the mix manifold.

In another aspect, the second airflow sub-circuit further comprises at least one second airflow sub-circuit ozone converter located proximate to the at least one flight deck cabin airflow inlet.

In another aspect, the at least one first airflow sub-circuit second ozone converter is located proximate to at least one of the at least one passenger cabin airflow inlets.

In another aspect, the at least one first airflow sub-circuit second ozone converter is located proximate to more than one of the plurality of passenger cabin airflow inlets.

In a further aspect, the at least one first airflow sub-circuit second ozone converter is located at each of the plurality of passenger cabin airflow inlets.

In another aspect, the first airflow sub-circuit further comprises at least one first airflow sub-circuit second ozone converter located proximate to at least one auxiliary recirculation fan.

In a further aspect, the at least one first airflow sub-circuit second ozone converter is located proximate to more than one of the plurality of passenger cabin airflow inlets.

In another aspect, the at least one first airflow sub-circuit second ozone converter is in communication with at least one of the plurality of passenger cabin airflow inlets.

In another aspect, the first airflow sub-circuit further includes a first airflow sub-circuit second ozone converter located proximate to and downstream of at least one auxiliary recirculation fan.

In another aspect, the at least one first airflow sub-circuit first ozone converter located upstream of the at least one air conditioning pack is in direct communication with a high-temperature airflow.

In another aspect, at least one of the second airflow sub-circuit and the first airflow sub-circuit further includes at least one second airflow sub-circuit ozone converter located proximate to and downstream from the at least one air conditioning pack and further located upstream from the mix manifold.

A further aspect is directed to an aircraft including at least one of the presently disclosed air purification systems.

According to a further aspect, a method for reducing ozone concentration from an aircraft is disclosed (e.g., including increasing ozone concentration reduction for existing systems) that includes providing a first airflow sub-circuit in an aircraft air management system, with the first airflow sub-circuit configured to deliver a first conditioned airflow to a passenger cabin, and with the first airflow sub-circuit including at least one first airflow sub-circuit first ozone converter, with the at least one first airflow sub-circuit first ozone converter comprising a first ozone reducing material (e.g., a first, or existing catalyst/sorbent "type"), with the at least one first airflow sub-circuit first ozone converter located upstream of or coincident with at least one air conditioning pack. The first airflow sub-circuit further includes at least one first airflow sub-circuit second ozone converter, with the at least one first airflow sub-circuit second ozone converter including at least one of a second ozone reducing material and a second VOC reducing material, with the at least one first airflow sub-circuit second ozone converter located downstream of the at least one air conditioning pack. The method further includes providing a second airflow sub-circuit in the aircraft air management system, with the second airflow sub-circuit configured to deliver a second conditioned airflow to a flight deck cabin, with the second airflow sub-circuit configured to exclude entry of conditioned air from the first airflow sub-circuit into the second airflow sub-circuit, with the second airflow sub-circuit including at least one second airflow sub-circuit ozone converter, with the at least one second airflow sub-circuit ozone converter including at least one of the second ozone reducing material and the second VOC reducing material, and with the at least one second airflow sub-circuit ozone converter located downstream of the at least one air conditioning pack. According to a present aspect, at least one of the second ozone reducing material and the second VOC reducing material is different from the first ozone reducing material.

In another aspect, a method further includes providing a mix manifold in communication with the first airflow sub-circuit and positioning at least one second ozone converter downstream of the mix manifold.

In another aspect, a method further includes disposing an auxiliary airflow sub-circuit in communication with the passenger cabin, with the auxiliary airflow sub-circuit configured to deliver an auxiliary airflow to a passenger cabin, with the auxiliary airflow sub-circuit comprising at least one auxiliary recirculation fan configured to direct the auxiliary airflow, with the auxiliary airflow in communication with at least one passenger cabin auxiliary inlet, and wherein the auxiliary airflow sub-circuit is not in ducted communication with the mix manifold.

In another aspect, a method further comprises disposing an auxiliary airflow sub-circuit in communication with the passenger cabin, with the auxiliary airflow sub-circuit configured to deliver an auxiliary airflow to a passenger cabin, with the auxiliary airflow sub-circuit including at least one auxiliary recirculation fan configured to direct the auxiliary airflow, with the auxiliary airflow in communication with at least one passenger cabin auxiliary inlet, and wherein the auxiliary airflow sub-circuit is not in ducted communication with the mix manifold.

In another aspect, a method further includes disposing at least one second airflow sub-circuit ozone converter proximate to and downstream of the at least one auxiliary recirculation fan.

In another aspect, a method further includes disposing at least one second airflow sub-circuit ozone converter proximate to and downstream of the at least one auxiliary recirculation fan, with no second airflow sub-circuit ozone converter positioned upstream of the mix manifold.

In a further aspect, a method further includes disposing at least one second airflow sub-circuit ozone converter proximate to and downstream of the auxiliary recirculation fan, with at least one second airflow sub-circuit ozone converter positioned upstream of the mix manifold.

In another aspect, a method is disclosed, with the method disclosing modifying an existing aircraft air management system to decrease ozone concentration in an aircraft interior with the existing aircraft management system including a first airflow sub-circuit configured to condition air for delivery into a passenger cabin air volume, with the first airflow sub-circuit comprising at least one first airflow sub-circuit first ozone converter, and with the at least one first airflow sub-circuit first ozone converter containing a first ozone reducing material. In a further aspect, the air management system further includes a mix manifold in communication with at least one air conditioning pack, and with at least one air conditioning pack positioned upstream of the mix manifold. The method further includes introducing at least one second ozone converter to the first airflow sub-circuit, with the at least one second ozone converter containing at least one of a second ozone reducing material and a second VOC reducing material, and introducing a second airflow sub-circuit to the existing air management system, with the second airflow sub-circuit configured to deliver an air supply into a flight deck air volume, with the second airflow sub-circuit comprising at least one second airflow sub-circuit second ozone converter including at least one of a second ozone reducing material and a second VOC reducing material, and the second airflow sub-circuit second ozone converter positioned in communication with and proximate to a flight deck air volume inlet. According to this method the at least one first airflow sub-circuit first ozone converter is positioned upstream of or coincident with the at least one air-conditioning pack, the at least one first airflow sub-circuit second ozone converter is positioned downstream of the at least one air-conditioning pack, and the first ozone reducing material is different from the at least one of a second ozone reducing material and a second VOC reducing material.

The features, functions and advantages that have been discussed can be achieved independently in various aspects or may be combined in yet other aspects, further details of which can be seen with reference to the following description and the drawings.

BRIEF DESCRIPTION OF THE DRAWINGS

Figure 1:
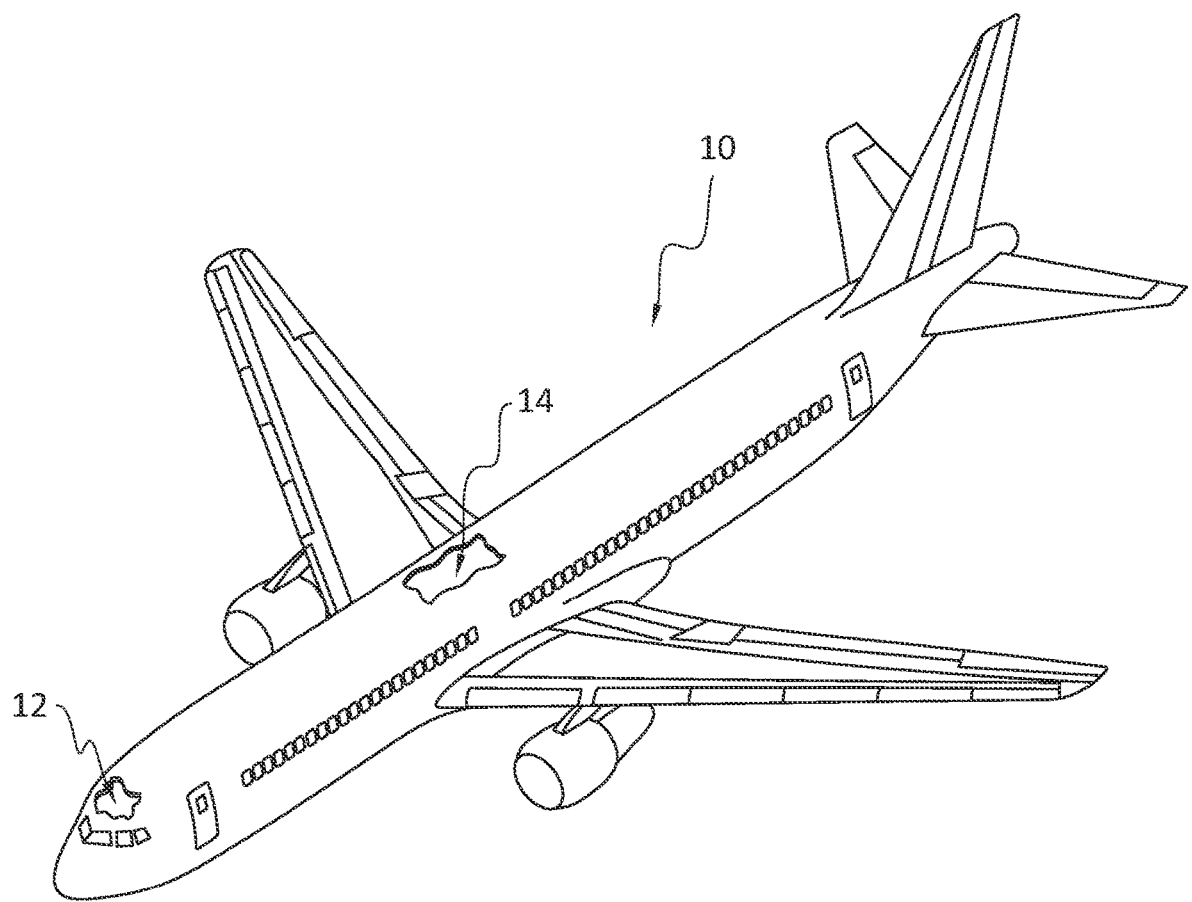
Figure 2:
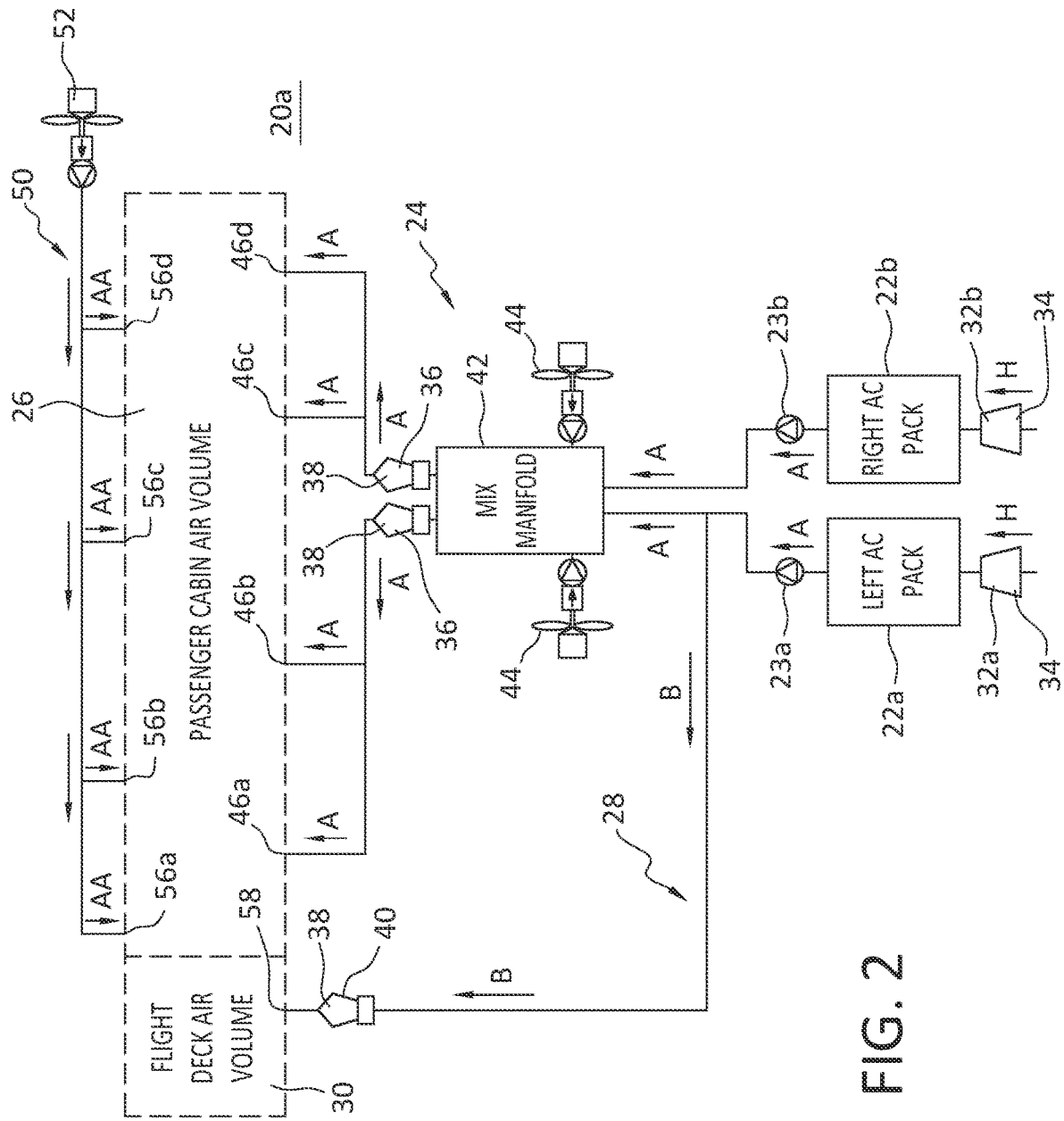
Figure 3:
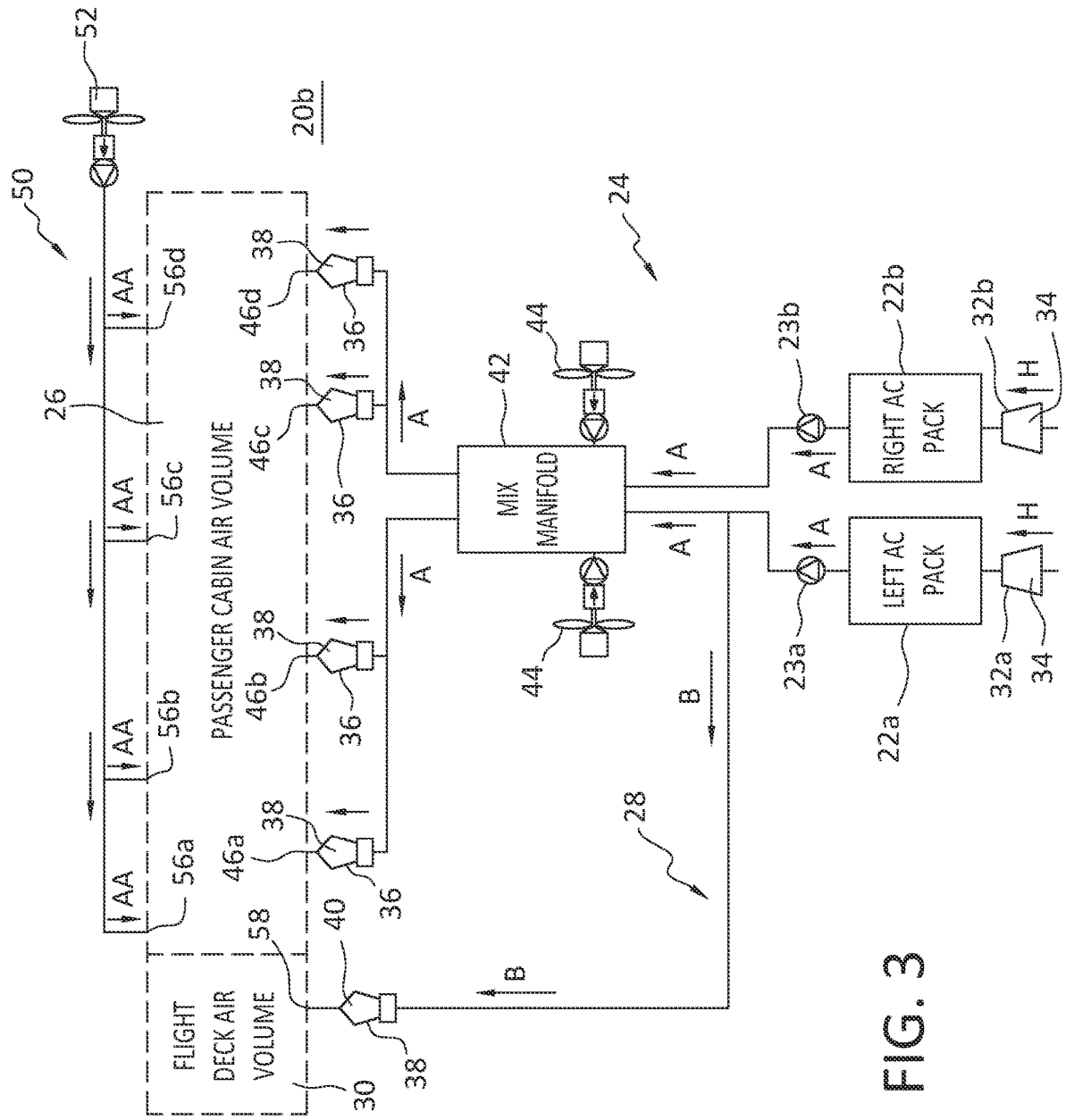
Figure 4:
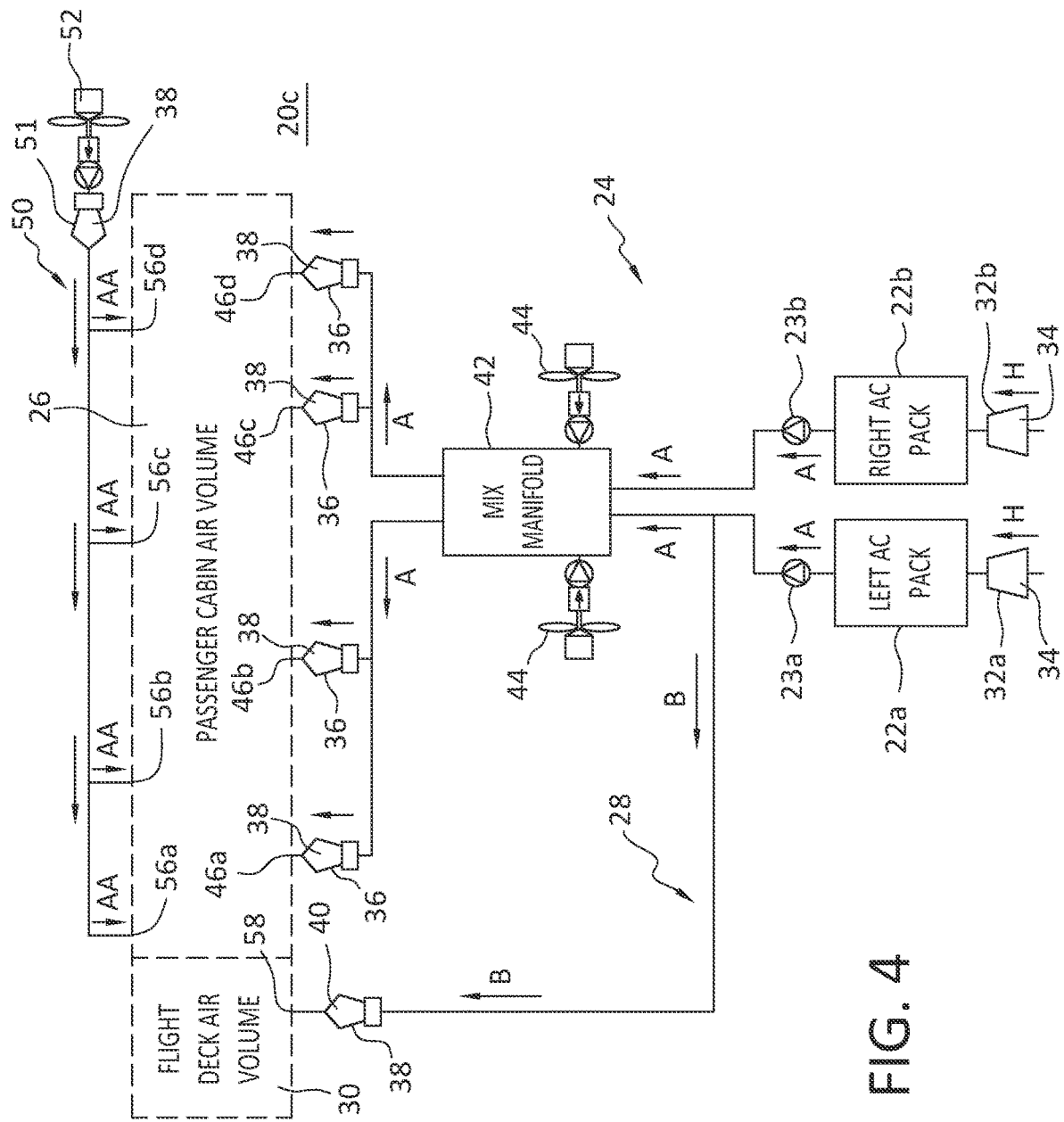
Figure 5:
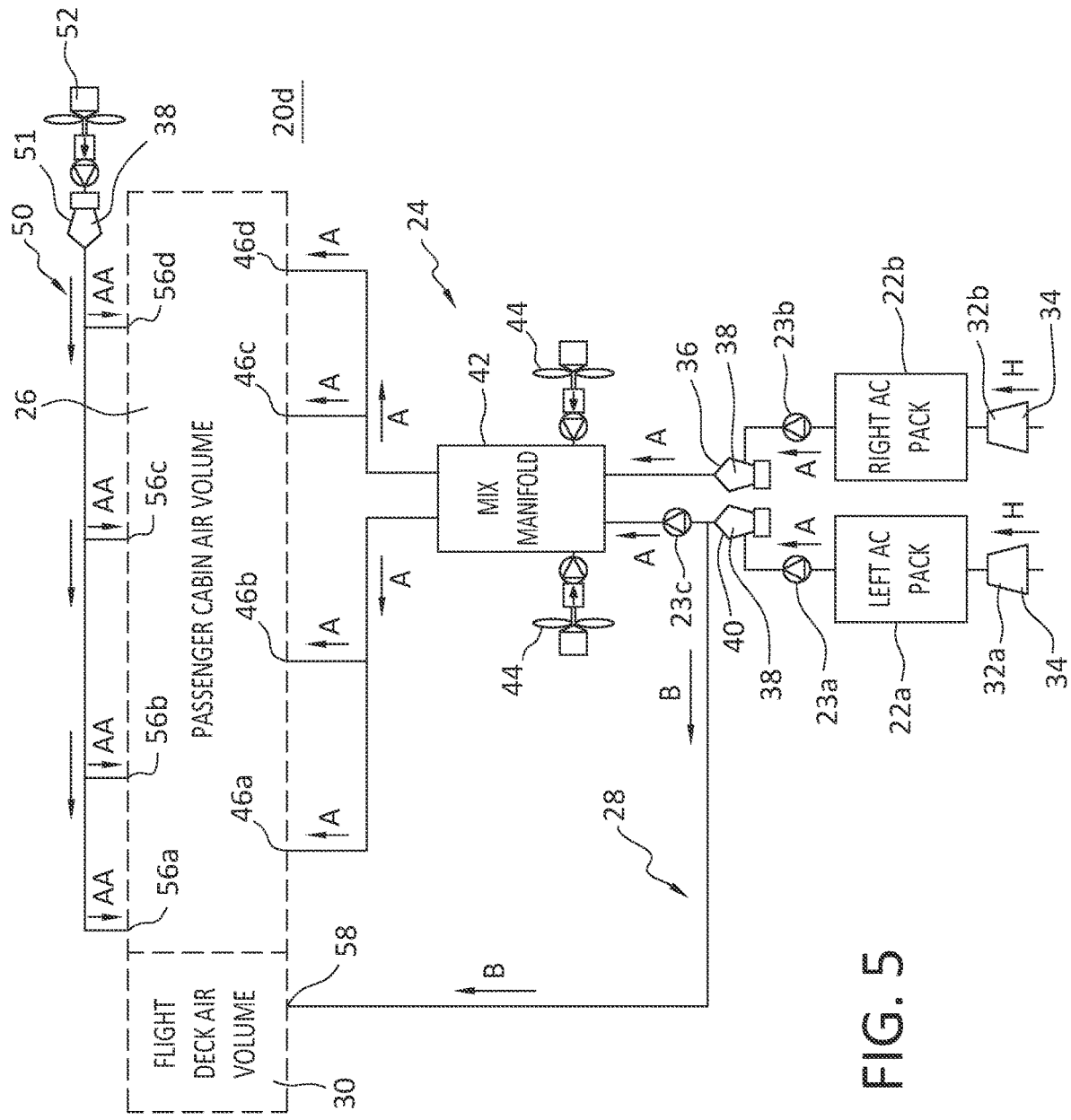
Figure 6:
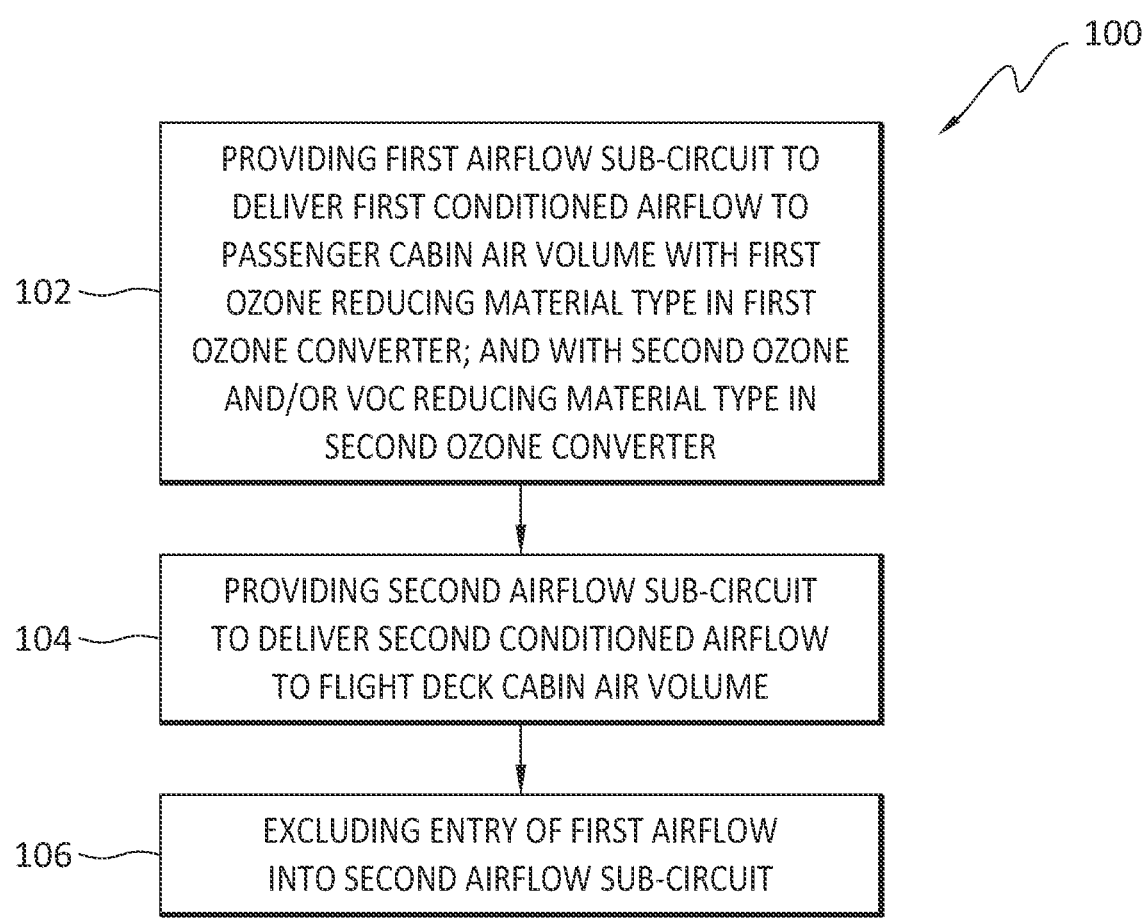
Figure 7:
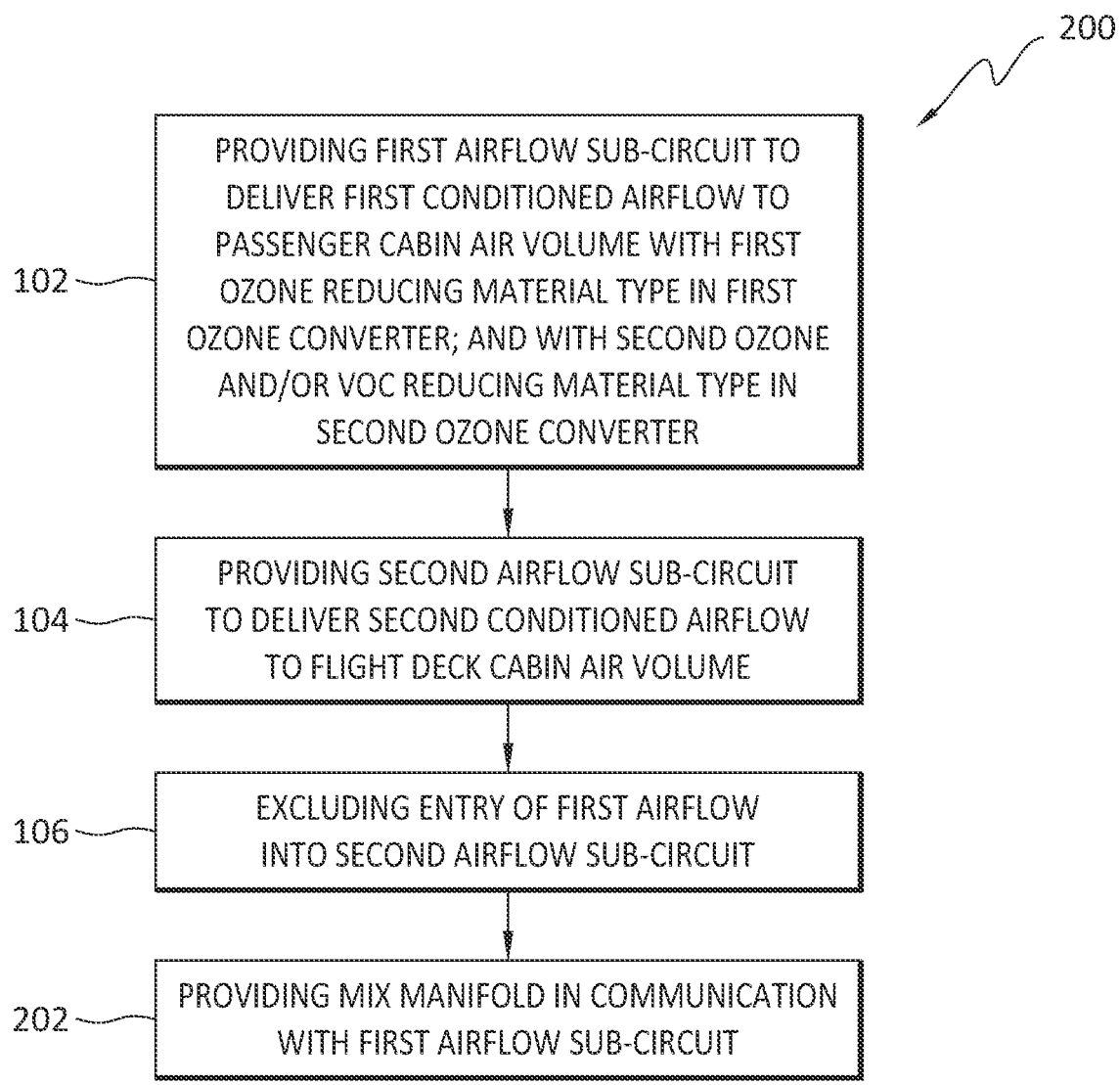
Figure 8:
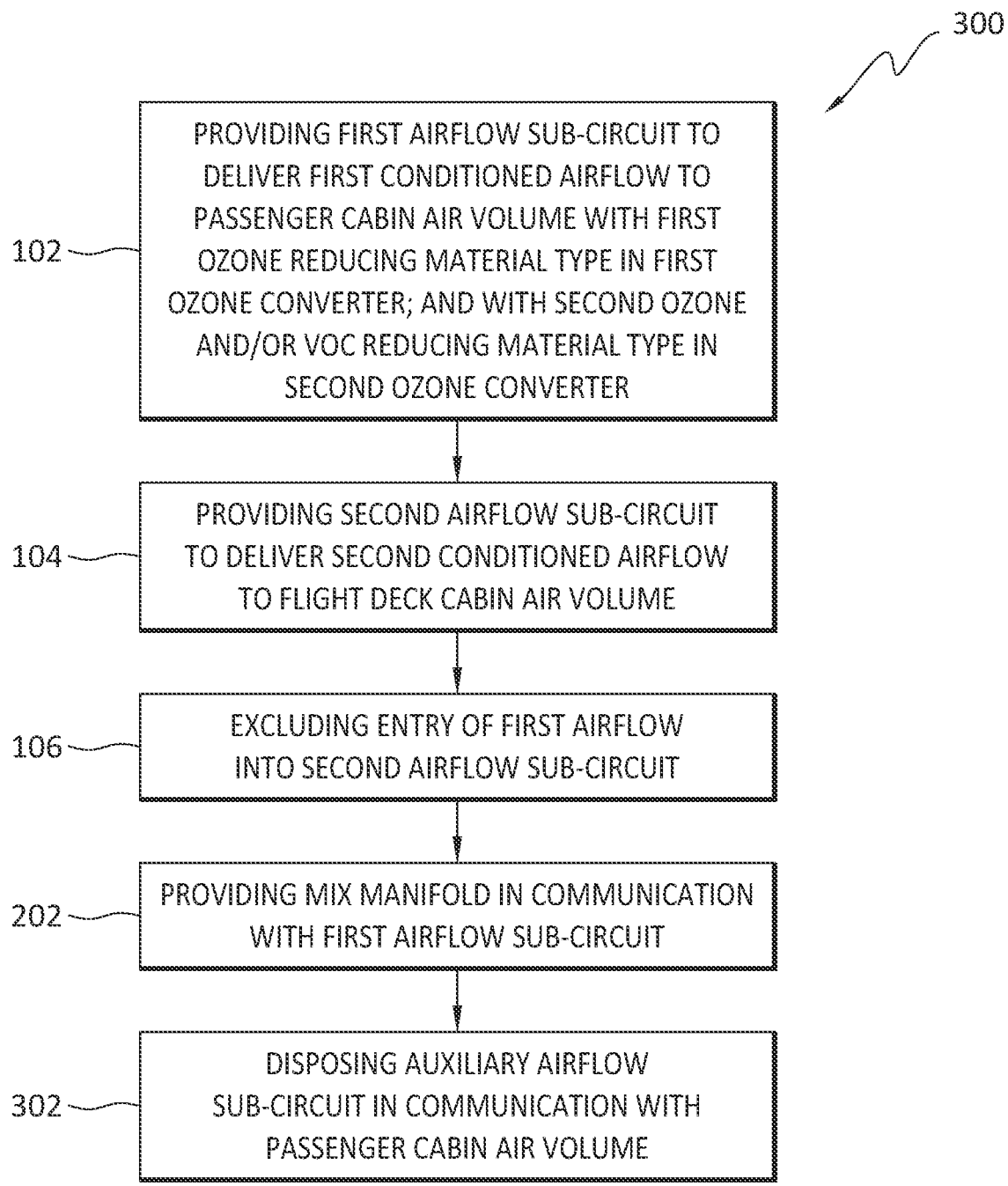
Figure 9:
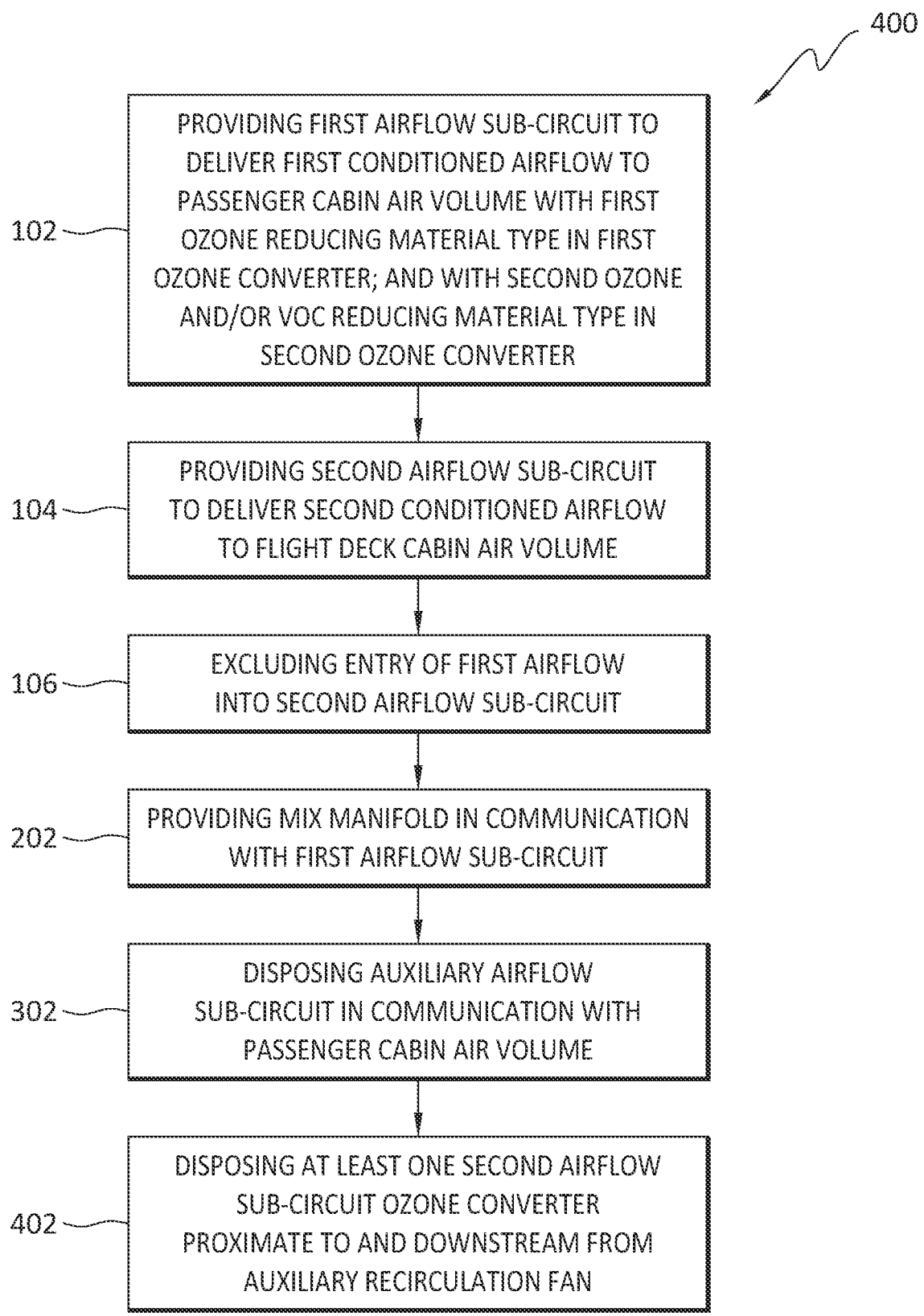

Having thus described variations of the disclosure in general terms, reference will now be made to the accompanying drawings, which are not necessarily drawn to scale, and wherein:

FIG. 1 is an illustration of a vehicle according to present aspects, with the vehicle shown in the form of an aircraft;

FIG. 2 is an illustration of a representative air management system architecture, according to present aspects;

FIG. 3 is an illustration of a representative air management system architecture, according to present aspects;

FIG. 4 is an illustration of a representative air management system architecture, according to present aspects;

FIG. 5 is an illustration of a representative air management system architecture, according to present aspects;

FIG. 6 is a flowchart outlining a method according to present aspects;

FIG. 7 is a flowchart outlining a method according to present aspects;

FIG. 8 is a flowchart outlining a method according to present aspects;

FIG. 9 is a flowchart outlining a method according to present aspects; and

Figure 10:
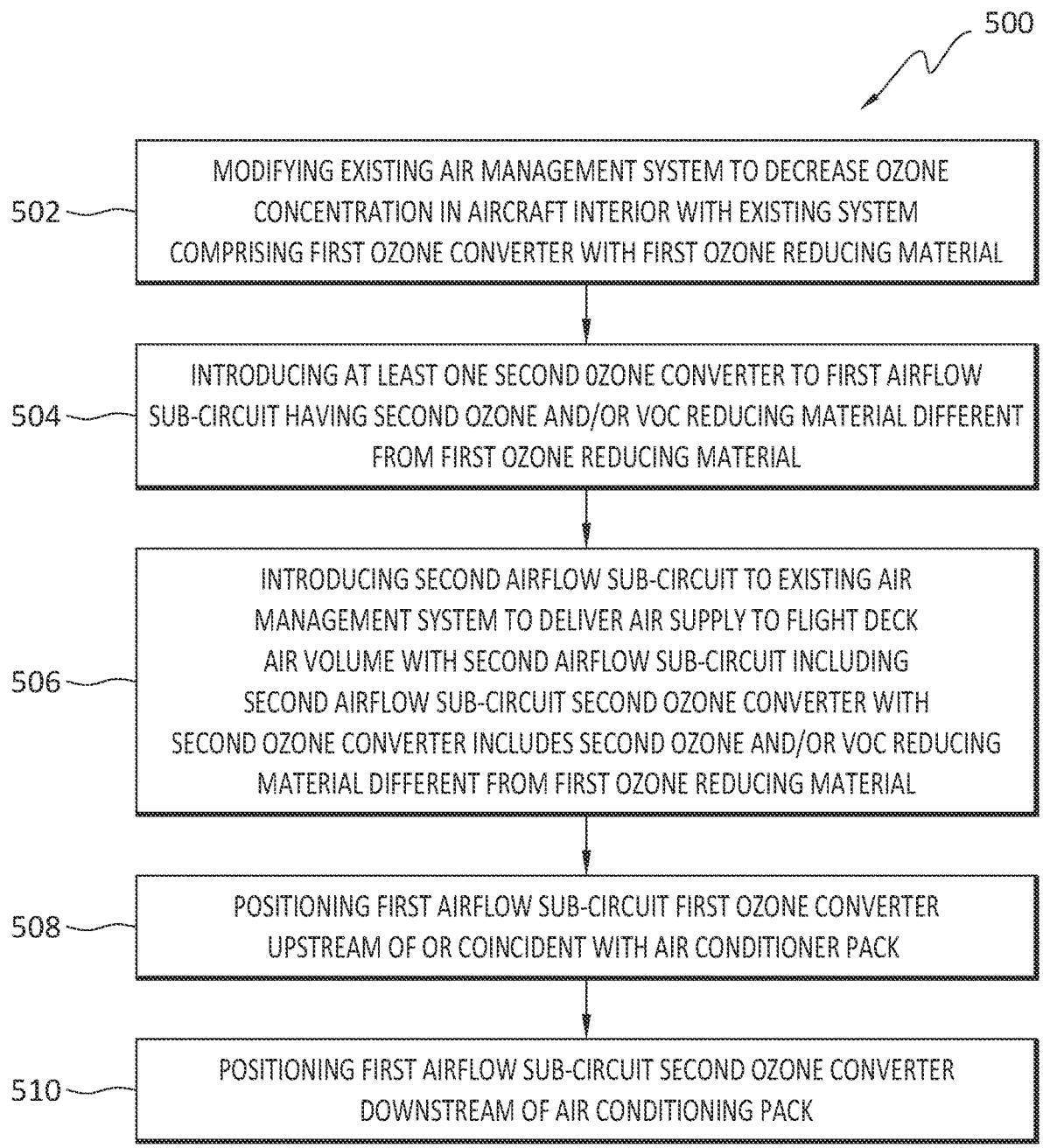

FIG. 10 is a flowchart outlining a method according to present aspects.

DETAILED DESCRIPTION

Present aspects disclose the use of and selected positioning of multiple "second" ozone reducing converters positioned throughout an air management system architecture (e.g., in multiple predetermined physical locations within the air management system architecture), and at locations that are located downstream of air conditioning packs. The multiple "second" ozone reducing converters are understood to be additional ozone converters with respect to "first" ozone converters that may typically exist in aircraft air management systems, and that are located upstream of or coincident with air conditioning packs. According to present aspects, the "second" ozone converters contain selected ozone reducing catalyst compositions (also equivalently referred to herein as "ozone reducing catalyst material") and/or multiple selected ozone reducing catalyst material types that are selected to differ with respect to the ozone reducing catalyst materials contained in the "first" ozone converters.

At altitudes at which commercial aircraft typically execute the flight segment (e.g., known as "cruise"), passenger cabin air volumes within the aircraft passenger cabin and flight deck air volumes within the flight deck can contain atmospheric levels of gaseous ozone that can irritate passengers and crew. An aircraft's air management system is responsible for conditioning ambient air intake and allocating and supplying an airflow to aircraft compartments (e.g., cabins, etc.). As a result, commercial airplanes typically include a means to ensure that concentrations of ozone (that, left unabated, may reach approximately 1.3 ppm ozone by volume at sea level equivalent) within the occupied areas of the aircraft cabin are maintained within ozone concentration levels considered to be "safe" ozone concentration levels.

According to present aspects, one recognized "safe" ozone concentration threshold for an aircraft cabin interior is a maximum ozone concentration (at "cruise") of about 0.25 parts per million ozone by volume (adjusted for sea level and referred to herein as "ppm ozone by volume—sea level equivalent"). Such an observed "safe" ozone concentration level below about 0.25 parts per million ozone (and that, for a three-hour time-weighted average, does not exceed 0.1 ppm by volume at sea level equivalent), represents an ozone concentration in an airflow environment within an aircraft cabin interior "at cruise" that is considered not likely to cause discomfort or irritation to humans. (See, e.g., 14 C.F.R. § 25.832).

In addition, most modern passenger airliners employ a minimum number of (e.g., typically no more than two) ozone reduction devices that each contain the same singular ozone reducing catalyst material and the same ozone catalyst material type. In addition, the existing ozone reduction devices are typically positioned proximate to a high temperature air intake region and are further positioned upstream of or coincident with existing air conditioning packs. Such locations can be difficult to access within the airplane's air management system.

Existing ozone reduction devices in passenger aircraft air management systems rely on the use of, and each device typically contains, the same catalyst material (e.g., the substance that "breaks down" or chemically "converts" ozone to ozone byproducts that are not harmful to humans). Many of the existing ozone reducing catalyst materials in use for this purpose are susceptible to performance losses resulting from, for example, exposure to interfering gaseous compounds in the ambient environment such as, for example, volatile organic compounds (VOCs), and other compounds (e.g., sulfur dioxide). As a result of interfering compound degradation of catalyst material, ozone reducing catalyst materials must be regularly removed from the airplane and cleaned, increasing airline workload, resulting in cost burdens to airlines, and/or increasing the time that an aircraft may be out-of-service, etc. Further, if catalyst degradation of an ozone reducing catalyst does occur (e.g., without proper cleaning and/or replacement, etc.), then aircraft passenger cabin ozone levels may rise to unacceptable or otherwise undesirable ozone concentration levels.

Typical existing ozone reduction solutions in contemporary commercial aircraft have relied on ozone reduction devices located upstream of air conditioning packs and that are often positioned in locations within an aircraft air management system architecture that are difficult to access (e.g., for mandatory replacement, reconditioning, etc.), and such existing ozone reduction devices typically present complete uniformity relative to active ozone reducing catalyst materials that are used by and present within such typical devices.

Also, the typical aircraft air purification systems are in communication with recirculation fans that do not supply airflow to the flight deck; a regulatory requirement that sequesters passenger cabin airflow from a flight deck airflow (with the flight deck typically configured to receive 100% airflow that is separate from passenger cabin airflow). Accordingly, present aspects also contemplate and otherwise facilitate an increased and enhanced ozone concentration reduction, as well as a VOC concentration reduction within a flight deck, and within the airflow that is intended for, and otherwise exclusively directed to, a flight deck. That is, according to present aspects, the presently disclosed methods, apparatuses, and systems will afford a significant improvement for ozone reduction and/or VOC reduction from airflow that will reach flight deck occupants and crew.

According to present aspects, new and modified air purification architectures present solutions for ensuring and maintaining safe levels of cabin ozone present in aircraft airflows. According to present aspects, multiple additional ozone reducing devices are intentionally positioned at various selected locations within an aircraft air management system architecture, and with the additional ozone reducing and/or VOC reducing devices containing and employing ozone removal catalysts and/or VOC removal catalysts that differ, and catalyst types that differ, from the catalysts and catalyst types used in existing ozone removal devices.

In addition, present aspects disclose significant ozone reduction system enhancements and efficiencies for delivering an airflow having at least one of reduced ozone concentrations and reduced VOC concentration to passenger aircraft cabin air volumes and also deliver an airflow having at least one of reduced ozone concentrations and reduced VOC concentration to flight deck air volumes.

Further present aspects are directed to apparatuses, systems, and methods for the reduction of ozone concentration by providing a predetermined and selected placement of additional (referred to herein as "second") ozone-removing devices within airflow sub-circuits in an aircraft that may already exist, while also treating an ozone-containing airflow with a plurality of differing ozone-reducing catalysts contained within the newly added and additional, "second", ozone-reducing devices.

According to present aspects, the selected physical locations in an aircraft air management system of the additional ozone reducing devices, according to present aspects, results in a change to the composition of the interfering compounds within and along an airflow within the augmented air management system. This present aspect has the beneficial effect of making the new ozone reducing devices less susceptible to the same degradation modes of the existing upstream devices that can be found on a typical air management system. This beneficial effect is further enhanced by the fact that the new devices' catalyst type selected for use in the presently disclosed ozone reducing devices is selected to have a different chemical makeup, and this offers a susceptibility profile that is unique to that of the existing upstream ozone reducing device. Further, the ozone removal capabilities of the supplemental ozone reducing devices disclosed herein reduce the performance burden of the existing upstream devices. This allows the catalyst density of the existing devices to be reduced and results in lower internal system pressure drops and commensurate ventilation, pressurization, and temperature control capacity improvements. Additionally, the reduced performance burden on the existing upstream devices could allow their cleaning intervals to undergo beneficial extensions.

By way of example, with respect to present aspects' improvements in reducing or eliminating, for example, pressure drops across an aircraft air management system, the following is provided as a non-limiting example. In a typical or existing air management system (e.g., an aircraft air management system that does not have the second converters disclosed herein), the amounts of ozone reducing material in the typical first airflow sub-circuit first ozone converter positioned upstream of or coincident with the air conditioning packs exhibit a pressure drop of about 1.0 psi per upstream unit over the first airflow sub-circuit when the existing, first ozone converter contains, for example, a catalytic slurry density (e.g., a mixture of catalyst and bonding agent) of about 150 g/L. The catalytic slurry density provided in the typical system is required to provide the desired minimum system efficiency of 85%. According to present aspects, when a second converter, or pair of second converters, or more, are placed online into the aircraft air management system, the added second converter units (each unit comprising a second catalyst or second catalyst type that is different from the catalyst in the first ozone converter) have a pressure drop of less than 0.25 psi on the system while increasing ozone removal efficiency of the system to 94%, and while allowing the original/existing/typical upstream ozone removal units to perform at a lower minimum efficiency of 75%. According to present aspects, reducing the ozone removal burden of the existing upstream units allows for a decreased amount of first catalyst material used in the existing upstream units that, in turn, allows the entire air management system architecture to exhibit a decrease in the overall system pressure drop of about 50% of the current pressure drop baseline over the entire air management system. Alternatively, the upstream/existing units' catalyst densities could remain the same in combination with the presently added downstream units having the same effectiveness as described above. The result would be an increase in total system pressure drop by 25%; but with a cleaning interval improvement for the upstream units of 75% greater than the baseline cleaning interval.

Present aspects further increase commercial airliner air management system efficiencies and capacities for performing ventilation, cabin pressurization, and temperature control functions, including, for example, the high temperature air performance of current typical catalyst materials, etc. According to present aspects, alternative catalyst materials that do not, at least in part, rely on high temperature air can be used, including catalysts that confer efficiencies to the present systems in the absence of high temperature air. In addition, the apparatuses, systems, and methods disclosed herein, and according to present aspects, are configured to locate multiple ozone reducing converters at selected physical locations that can be more easily accessed for reducing maintenance and cost burdens on airlines (e.g., ozone reduction device cleaning efficiencies will be improved as the cleaning and maintenance intervals can be extended, etc.).

FIG. 1 is a representative illustration of a vehicle 10 in the form of an aircraft, with the vehicle 10 (e.g., the aircraft, etc.), having interior regions that can be inhabited by, for example, passengers and/or crew that could benefit from an improved purified and circulated airflow having a reduced ozone concentration, as well as a reduced volatile organic compound (VOC) concentration in the purified and circulated airflow. As shown in FIG. 1, the vehicle 10 comprises a passenger cabin 14 and a flight deck 12 (e.g., a flight deck cabin).

FIGS. 2, 3, 4, and 5 are representative non-limiting drawings of presently contemplated airflow treatment architectures according to present aspects. As shown in FIGS. 2, 3, 4, and 5, air purification systems are configured to increase ozone conversion or, stated another way, to reduce at least one of ozone concentration and/or VOCs in conditioned air that is recirculated to a passenger cabin and to further treat air delivered to a flight deck for the purpose of reducing ozone concentration and/or VOCs from an airflow that is directed to a flight deck. According to present aspects, "recirculated air" is a term that includes conditioned air that is delivered to an aircraft cabin environment.

According to present aspects the ozone reduction components (e.g., ozone converters) placement is different from existing systems and architectures that may treat and reduce ozone concentration; but do so less efficiently than the systems and architectures according to presently disclosed aspects. In addition, the reactive materials (sorbents, reagents, etc.) contained within various ozone converters that are advantageously-located within an airflow circuit are reactive materials that are different from any reagents that may be found in conventional ozone treatment components in existing air purification systems. Further, FIGS. 2, 3, 4, and 5 represent presently contemplated airflow system architectures useful in a vehicle, for example, of the type shown in FIG. 1.

FIG. 2 shows a representative and presently contemplated air purification system 20a, according to a present aspect, with air purification system 20a comprising enhanced ozone concentration reducing capabilities (e.g., the further reduction of an ozone concentration in an airflow to a predetermined reduced ozone concentration and/or removal of ozone from an airflow). As shown in FIG. 2, air purification system 20a comprises an architecture that can deliver a conditioned airflow to a passenger cabin air volume 26 and to a flight deck air volume 30. As shown in FIG. 2, an airflow, that can be a heated airflow as indicated by Arrow "H" can enter or otherwise be directed and introduced to air purification system 20a via an inlet or intake that can encounter a first airflow sub-circuit first ozone converter. A first airflow sub-circuit 24 for directing a first conditioned airflow "A" is shown in FIG. 2 as comprising components for directing first conditioned airflow A to a passenger cabin air volume 26.

As shown in FIG. 2, a first airflow sub-circuit first ozone converter 32a containing a first ozone reducing material 34 is in communication with and upstream of "left" air conditioning (AC) pack 22a. Further, a first airflow sub-circuit first ozone converter 32b containing a first ozone reducing material 34 is in communication with and upstream of "right" air conditioning (AC) pack 22b. The left and right air conditioning packs 22a. 22b condition the introduced airflow "H", condition the admitted airflow "H", and release a first conditioned airflow "A" from air conditioning packs 22a, 22b in a downstream direction from the air conditioning packs 22a, 22b and toward a mix manifold 42. Recirculation fans 44 are shown in communication with and otherwise positioned adjacent the mix manifold 42 to further direct a desired airflow through air purification 20a, through and out from mix manifold 42 and toward a pair of first airflow sub-circuit second ozone converters 36 located downstream of the mix manifold 42. As shown in FIG. 2, a pair of first airflow sub-circuit second ozone converters 36 located downstream of the mix manifold 42 each contain at least one of a second ozone reducing material and a second VOC reducing material 38, with the at least one of a second ozone reducing material and a second VOC reducing material selected to differ from the first ozone reducing material 34 located within the first airflow sub-circuit first ozone converters 32a, 32b that are located upstream of the left and right air conditioning packs 22a, 22b, respectively.

While FIG. 2 shows the first airflow sub-circuit first ozone converters 32a, 32b located upstream of the left and right air conditioning packs 22a, 22b, respectively, it is understood that, according to present aspects, architecture design may instead locate the first airflow sub-circuit first ozone converters 32a, 32b coincident with or integrated within conditioning packs 22a, 22b. Although not shown in FIG. 2, present aspects contemplate that the first airflow sub-circuit first ozone converters 32a, 32b also can be positioned within the first sub-circuit architecture in an orientation that is coincident with the left and right air conditioning packs 22a, 22b, respectively, and/or the first airflow sub-circuit first ozone converters 32a, 32b also can be positioned within the first sub-circuit architecture in an orientation where the first airflow sub-circuit first ozone converters 32a, 32b are integrated into or are otherwise integral with the left and right air conditioning packs 22a, 22b, respectively.

As further shown in FIG. 2, first airflow sub-circuit 24 further comprises a pair of first airflow sub-circuit second ozone converters 36 positioned downstream of, in communication with, and proximate to the mix manifold. The pair of first airflow sub-circuit second ozone converters 36 are configured to contain amounts of at least one of a second ozone reducing material and a second VOC reducing material 38 that can be at least one of a reducing material, catalyst, sorbent, etc., as will be described more fully herein. The at least one of a second ozone reducing material and a second VOC reducing material 38 contained within the first airflow sub-circuit second ozone converters 36 is selected to be a different material from the first ozone converting material 34 contained within first airflow sub-circuit first ozone converters 32a, 32b. As further shown in FIG. 2, first conditioned airflow "A" that has passed through and that exits from the pair of first airflow sub-circuit second ozone converters 36 continues through the first airflow sub-circuit 24 with first conditioned airflow "A" directed into passenger cabin air volume 26 via passenger cabin airflow inlets 46a, 46b, 46c, 46d.

According to prevailing regulations, or desired performance enhancements, the flight deck air volume delivered into a flight deck for consumption of flight deck occupants is typically delivered via an airflow sub-circuit that is separate and distinct from the air delivered to a passenger cabin as a passenger cabin air volume. Accordingly, FIG. 2 further shows a second airflow sub-circuit 28 that is dedicated to the delivery of a second conditioned airflow "B" to a flight deck air volume 30 in a flight deck cabin. As shown in FIG. 2, first conditioned airflow "A" that emerges or is otherwise directed from the left air conditioning pack 22a is split, with a portion of first conditioned airflow "A" continuing within the first airflow sub-circuit 24 and having a destination within the passenger cabin air volume 26, while a portion of first conditioned airflow "A" is directed into the second airflow circuit 28 and is labeled as second conditioned airflow "B". As shown in FIG. 2, bulkhead check valves 23a, 23b can respectively check the airflow "A" released by the left and right air conditioning packs 22a, 22b, or check high pressure from the cabin that reverses flow back into the conditioning packs in the event of a pack failure (e.g., a pack duct burst to ambient, etc.). Present aspects contemplate the further incorporation of various valves and flow controls throughout the air purification system 20a (although not shown in FIG. 2), including, for example, various one-way valves or other mechanisms that achieve a one-way directional and restricted airflow can be employed to achieve the directed airflow that transforms a portion of first conditioned airflow "A" to become second conditioned airflow "B" that is destined for introduction into the flight deck air volume 30 via the second airflow sub-circuit 28.

As shown in FIG. 2, second conditioned airflow B is further directed within second airflow sub-circuit 28 to second airflow sub-circuit second ozone converter 40, with second airflow sub-circuit second ozone converter containing an amount of at least one of a second ozone reducing material and a second VOC reducing material 38, with second ozone reducing material selected to differ from the first ozone reducing material 34 contained within first airflow sub-circuit first ozone converter 32*a*. Second conditioned airflow "B" is then directed through second airflow sub-circuit second ozone converter 40 where a further predetermined ozone reduction in second conditioned airflow "B" is conducted.

The emergent second conditioned airflow "B" released from second airflow sub-circuit second ozone converter is then directed into the flight deck air volume 30 via at least one flight deck cabin airflow inlet 58. In this way, as shown in FIG. 2, a conditioned airflow ("B") is directed to a flight deck cabin that that is separate from the conditioned airflow ("A") that is directed to the passenger cabin. The air purification system 20*a* shown in FIG. 2 is shown as conducting a second ozone treatment of airflow "A" and airflow "B" by placing, in a predetermined fashion within an air management architecture, additional or second ozone converting apparatuses (e.g., second ozone converters) within the first and second airflow sub-circuits positioned at predetermined locations that are downstream from air conditioning packs, with the predetermined locations selected to facilitate removal that can facilitate maintenance or replacement. Further, the second ozone converting apparatuses contain at least one of a second ozone reducing material and a second VOC reducing material that is intentionally selected to be different from the first ozone reducing material contained within the first ozone converters that are located upstream of or coincident with the air conditioning packs.

As further shown in FIG. 2, an auxiliary airflow sub-circuit 50 that can comprise, for example, at least one auxiliary recirculation fan, can direct an auxiliary airflow "AA" into the passenger cabin air volume 26 via passenger cabin auxiliary airflow inlets 56*a*, 56*b*, 56*c*, 56*d*.

An alternative present aspect contemplates a further air purification system 20*b* with enhanced ozone and/or VOC reducing capabilities (e.g., the further reduction of an ozone concentration in an airflow) and is shown in FIG. 3. As shown in FIG. 3, many of the components shown and described (with similar numbering) as air purification system 20*a* as shown in FIG. 2 are again present in the alternative air purification system 20*b* shown in FIG. 3, with at least one difference between air purification systems 20*a* (shown in FIG. 2) and 20*b* (shown in FIG. 3) involving the positioning of and number of the second airflow subcircuit second ozone converters 36 within the first airflow sub-circuit 24. As shown in FIG. 3, air purification system 20*b* comprises the second conditioned airflow "B" directed to the flight deck air volume via the second airflow sub-circuit 28 can be the same or substantially the same as shown in air purification system 20*a* as shown in FIG. 2. As further shown in FIG. 3, air purification system 20*b* comprises the auxiliary airflow sub-circuit 50 that can comprise, for example, an auxiliary recirculation fan, and that can direct an auxiliary airflow "AA" into the passenger cabin air volume 26. That is, the auxiliary airflow sub-circuit 50 shown in air purification 20*b* can be the same or substantially the same as the auxiliary airflow sub-circuit 50 shown in air purification 20*a* as shown in FIG. 2.

As shown in FIG. 3, air purification system 20*b* comprises one or more first airflow sub-circuit second ozone converters 36 positioned downstream of the mix manifold 42 and are further positioned proximate to or otherwise adjacent to one or more of the passenger cabin airflow inlets 46*a*, 46*b*, 46*c*, 46*d*. By positioning the one or more first airflow sub-circuit second ozone converters 36 adjacent to the one or more of the passenger cabin airflow inlets 46*a*, 46*b*, 46*c*, 46*d*, the first airflow sub-circuit second ozone converters 36 selectively located more accessibly within the architecture of the air purification system 20*b*, at least with respect to facilitating removal, cleaning, maintenance, installation, re-installation, etc. of the one or more first airflow sub-circuit second ozone converters 36. The one or more first airflow sub-circuit second ozone converters 36 contain an amount of at least one of a second ozone reducing material and a second VOC reducing material 38, with the second ozone reducing material 38 differing from the first ozone reducing material 34 contained in the first airflow sub-circuit first ozone converters 32*a*, 32*b*.

Although not shown in FIG. 3, present aspects contemplate that the first airflow sub-circuit first ozone converters 32*a*, 32*b* also can be positioned within the first sub-circuit architecture in an orientation that is coincident with the left and right air conditioning packs 22*a*, 22*b*, respectively, and/or the first airflow sub-circuit first ozone converters 32*a*, 32*b* also can be positioned within the first sub-circuit architecture in an orientation where the first airflow sub-circuit first ozone converters 32*a*, 32*b* are integrated into or are otherwise integral with the left and right air conditioning packs 22*a*, 22*b*, respectively.

Another alternative present aspect contemplates a further air purification system 20*c* with enhanced ozone and/or VOC reducing capabilities (e.g., the further reduction of an ozone concentration in an airflow) and is shown in FIG. 4. As shown in FIG. 4, many of the components shown and described (with similar numbering) as air purification system 20*a* and 20*b* as shown in FIGS. 2 and 3, respectively, are again present in the alternative air purification system 20*c* shown in FIG. 4, with at least one difference between air purification systems 20*b* (shown in FIG. 3) and 20*c* (shown in FIG. 4) involving the addition of auxiliary airflow sub-circuit ozone converter 51 containing an amount of at least one of a second ozone reducing material and a second VOC reducing material 38, with the auxiliary airflow sub-circuit ozone converter 51 positioned proximate to and downstream from the auxiliary airflow recirculation fan 52.

Although not specifically shown, in FIG. 4, present aspects further contemplate the placement of one or more auxiliary airflow sub-circuit ozone converters 51 positioned adjacent to, proximate to, or otherwise positioned in close communication with the passenger cabin auxiliary airflow inlets 56*a*, 56*b*, 56*c*, 56*d*. According to such aspects (not shown in FIG. 4), the placement of one or more auxiliary airflow sub-circuit ozone converters 51 positioned adjacent to, proximate to, or otherwise in close communication with the passenger cabin auxiliary airflow inlets 56*a*, 56*b*, 56*c*, 56*d* can obviate the need for the placement of the auxiliary airflow sub-circuit ozone converter 51 from a position proximate to the auxiliary airflow recirculation fan 52. Although not shown in FIG. 4, further present aspects contemplate positioning the one or more auxiliary airflow sub-circuit ozone converters 51 upstream of the auxiliary airflow recirculation fan 52, or coincident with the auxiliary airflow recirculation fan 52, or the one or more auxiliary airflow sub-circuit ozone converters 51 can be integrated into or otherwise integral with the auxiliary airflow recirculation fan 52.

By positioning the one or more auxiliary airflow sub-circuit ozone converters 51 adjacent to the one or more of the passenger cabin auxiliary airflow inlets 56*a*, 56*b*, 56*c*, 56*d*, the one or more auxiliary airflow sub-circuit ozone converters 51 can be located more accessibly within the architecture of the air purification system 20*c*, at least with respect to facilitating removal, cleaning, maintenance, installation, re-installation, etc. of the one or more auxiliary airflow sub-circuit ozone converter 51. Further, the one or more auxiliary airflow sub-circuit ozone converters 51 can each contain an amount of at least one of a second ozone reducing material and a second VOC reducing material 38, with the at least one of a second ozone reducing material and a second VOC reducing material 38 differing from the first ozone reducing material 34 contained in the first airflow sub-circuit first ozone converters 32a, 32b. Although not shown in FIG. 4, present aspects contemplate that the first airflow sub-circuit first ozone converters 32a, 32b also can be positioned within the first sub-circuit architecture in an orientation that is coincident with the left and right air conditioning packs 22a, 22b, respectively, and/or the first airflow sub-circuit first ozone converters 32a, 32b also can be positioned within the first sub-circuit architecture in an orientation where the first airflow sub-circuit first ozone converters 32a, 32b are integrated into or are otherwise integral with the left and right air conditioning packs 22a, 22b, respectively.

An alternative present aspect contemplates a further air purification system 20d with enhanced ozone reducing capabilities (e.g., the further reduction of an ozone concentration in an airflow) and is shown in FIG. 5. As shown in FIG. 5, many of the components shown and described (with similar numbering) as air purification system 20a, 20b, and 20c as shown in FIGS. 2, 3, and 4, respectively, are again present in the alternative air purification system 20d shown in FIG. 5.

FIG. 5 shows purification system 20d comprising the placement and positioning of second airflow sub-circuit second ozone converter 40 downstream of and proximate to left air conditioning pack 22a, and upstream of the mix manifold 42. This positioning of the second airflow sub-circuit second ozone converter 40 in air purification system 20d is in contrast to the positioning of the second airflow sub-circuit second ozone converter 40 being proximate to the flight deck cabin airflow inlet 58 as shown in air purification systems 20a (shown in FIG. 2), 20b (shown in FIG. 3), and 20c (shown in FIG. 4). In addition, in contrast to the air purification systems 20a, 20b, and 20c (shown in FIGS. 2, 3, and 4, respectively), FIG. 5 shows air purification system 20d comprising the placement and positioning of the first airflow sub-circuit second ozone converter downstream of and proximate to the right air conditioning pack 22b and upstream of the mix manifold 42. Depending on the dimensions of the object comprising the air purification system 20d (e.g., a vehicle such as, for example, an aircraft), the positioning of the first airflow sub-circuit second ozone converter 36 downstream of and proximate to the right air conditioning pack 22b and upstream of the mix manifold 42, and the positioning the second airflow sub-circuit second ozone converter downstream of and proximate to the left conditioning pack 22b and upstream of the mix manifold 42 can benefit the air purification system architecture, at least with respect to facilitating removal, cleaning, maintenance, installation, re-installation, etc. of the first and second airflow sub-circuit second ozone converters, 36 and 40, respectively, that, again contain an amount of at least one of a second ozone reducing material and a second VOC reducing material 38, with the second ozone reducing material 38 differing from the first ozone reducing material 34 contained in the first airflow sub-circuit first ozone converters 32a, 32b. Although not shown in FIG. 5, present aspects contemplate that the first airflow sub-circuit first ozone converters 32a, 32b also can be positioned within the first sub-circuit architecture in an orientation that is coincident with the left and right air conditioning packs 22a, 22b, respectively, and/or the first airflow sub-circuit first ozone converters 32a, 32b also can be positioned within the first sub-circuit architecture in an orientation where the first airflow sub-circuit first ozone converters 32a, 32b are integrated into or are otherwise integral with the left and right air conditioning packs 22a, 22b, respectively. In addition, FIG. 5 shows the placement of a check valve 23c that is positioned upstream of the mix manifold 42 and is further positioned downstream of the second airflow sub-circuit second ozone converter 40 such that airflow "B" can be diverted or split from airflow "A" and directed into the second airflow sub-circuit 28 that is directed to the flight deck air volume. Control valve can be any valve type that can be a one way valve that does not allow a back flow of air from airflow "A" from the first airflow sub-circuit airflow "A" to enter the second airflow sub-circuit airflow "B". Check valve 23c is further understood to be in communication with a system controller, and check valve 23c can be a valve that can receive signals sent remotely, and that can otherwise be operated in response to signals sent from a controller.

Although not shown in FIG. 5, further present aspects contemplate positioning the one or more auxiliary airflow sub-circuit ozone converters 51 upstream of the auxiliary airflow recirculation fan 52, or coincident with the auxiliary airflow recirculation fan 52, or the one or more auxiliary airflow sub-circuit ozone converters 51 can be integrate into or otherwise integral with the at least one auxiliary airflow recirculation fan 52.

According to present aspects, the first airflow sub-circuit first ozone converters represent ozone converters that may exist in current or typical aircraft air management systems. Such typical ozone converters can comprise first ozone reducing materials that comprise Pd-containing catalysts, Pt-containing catalysts, etc., and that can react with ozone and reduce ozone concentration in an airflow of an air management system. However, typical systems that typically employ one left-side and one right-side ozone converter typically use the same catalyst material. In addition, the amount of catalyst required in the existing types of ozone converter represents a degree of physical resistance to airflow in the air management system. These catalyst types previously in use also rely on high-temperature air in order to perform their ozone conversion functions, which can also increase power usage of the system or drive otherwise unnecessary high temperature airflow into the air management system. This has resulted in complications for the overall air management system including, for example, significant internal pressure drops across the air management system. Such pressure drops reduce the typical existing air management system efficiency and capacity for optimally performing required ventilation, cabin pressurization and temperature control functions, and can result in increased power usage to drive the air management systems.

The apparatuses, system, and methods disclosed herein contemplate incorporating (e.g., including into existing air management systems) additional "second" ozone converters into a first airflow sub-circuit (the circuit that is responsible for delivering a treated airflow to a passenger air volume). Present aspects further contemplate incorporating (e.g., including into existing air management systems) "second" ozone converters into an auxiliary airflow circuit (e.g., an auxiliary circuit responsible for delivering a treated airflow to a passenger air volume). Still further present aspects contemplate incorporating (e.g., including into existing air management systems) "second" ozone converters into a second airflow sub-circuit defined herein as the circuit responsible for delivering a treated airflow to a flight deck air volume. According to present aspects, the "second" ozone converters are each located downstream of air conditioning packs, and the "second" ozone converters comprise different ozone and/or VOC reducing catalyst materials than are present within existing or "first" ozone converters (e.g., the ozone converters that may be existing ozone converters, and that are positioned upstream of or coincident with air conditioning packs in an aircraft management system).

The present systems, according to present aspects provide significant enhanced system design flexibility, as placement of the "second" ozone converters comprising at least one of a second ozone reducing material and a second VOC reducing material can be dimensioned (e.g., can have a footprint) or otherwise configured to comport with space constraints across the design platforms of various aircrafts. That is, the presently disclosed air management systems can be installed as new systems, or the "second" ozone converters can be added to existing aircraft air management systems to retrofit and/or otherwise modify existing air management systems. According to present aspects, a selected number of "second" ozone converters are added into the first, second, or auxiliary airflow sub-circuits at locations within and along the airflow pathways (e.g., the airflow pathway ducted passageways, lines, piping, etc.) and downstream of air conditioning packs; and at locations that can be more easily accessed for maintenance, replacement (e.g., catalyst replacement, catalyst cartridge replacement, converter replacement, etc.).

In addition, according to present aspects, a significantly greater number of ozone converters are integrated into or are otherwise introduced into the present air management systems as compared with known existing systems. By increasing the number of integrated ozone converters, and by varying the positioning within the air management system of a greater number of converters to locations not currently known (e.g., all locations of which are downstream of the air conditioning packs), the present systems allow for the incorporation of "second" ozone converters that can have a reduced amount of ozone and/or VOC reducing material catalyst per ozone converter as compared to the amount of ozone reducing material traditionally contained with the existing ozone converters. According to present aspects, the reduction in amount of catalyst material used per ozone converter significantly reduces undesired pressure drops across the air management system, or substantially eliminates pressure drops across the air management system.

As stated herein, while Pd-containing and Pt-containing ozone-reducing catalysts can reduce and otherwise remove some VOCs from an airflow, such VOC capture by such metal-containing catalysts can impact the ability of such catalysts to reduce ozone, or can otherwise require the more frequent replacement, refreshing, etc. of the catalyst material within the ozone converters of the type located upstream of the manifold. According to present aspects, the intentional and selected use of a second ozone reducing catalyst and/or VOC reducing catalyst in the second converters that is different from the first ozone reducing material catalyst used in existing first ozone converters (e.g., the existing converters that are positioned upstream of the air conditioning packs, etc.) further increases system efficiencies of the present systems, at least by maintaining a greater percentage of the total catalyst volume that can be dedicated to ozone removal. Alternatively, present aspects further contemplate the intentional selection of differing ozone and/or VOC removal catalyst catalysts for the purpose of the second ozone converters both reducing ozone concentration and also reducing VOC concentration from an air management system airflow.

By way of non-limiting example, present aspects contemplate an air management system comprising first airflow sub-circuit first converters positioned upstream of the air conditioning packs with the first converters comprising amounts of first ozone reducing material that can be, for example, a Pd-containing-, Pt-containing-, Ni-containing or other metal-containing catalyst. When the aforementioned metal-containing catalysts are present as the first ozone reducing material in the first ozone converter, present aspects contemplate the selected positioning of a selected number second ozone converters at selected locations in the airflow subcircuits downstream of the air conditioning packs, with the second ozone converters comprising selected amounts of selected and differing second ozone and/or VOC reducing material, with the second ozone reducing material comprising at least one of: activated carbon, metal oxides, amines, zeolites, and combinations thereof.

Present aspects further contemplate the useful incorporation of selected manganese oxide ($MnO_x$)-based catalysts as at least the second ozone reducing material and/or VOC reducing material in the second ozone converters (e.g., $MnO_x$-based catalysts that can decompose ozone to oxygen preferably at room temperature, and that are typically lower cost materials, while possessing high catalytic activity).

Preferred second ozone and/or VOC reducing materials selected for use in the presently disclosed systems, apparatuses, and methods further include sorbents that have "high" specific surface area, with the term "high" specific surface area defined herein as a specific surface area greater than about 5000 $ft^2/g$. Such contemplated sorbents according to present aspects include, for example, activated carbon, zeolites, amines, metal organic frameworks, and combinations thereof, etc. The selected sorbents provide an arduous path for airflow that can enable unstable bonds with the ozone molecule to be cleaved by the reaction of ozone with a selected sorbent surface. Additional characteristics of suitable selected sorbents selected for use in the presently disclosed methods, systems, and apparatuses, and according to present aspects, include, for example, high sorption capacities, resistance to temperature, resistance to pressure, etc.

According to present aspects, sorbent formulations increase system efficiencies for ozone reduction that can reduce the total amount of "traditional" metal-based ozone reducing catalyst material (e.g., Pt-containing catalyst, Pd-containing catalyst, etc.), and that can simultaneously increase (e.g., by up to about a 50% reduction of existing metal-based ozone reducing catalyst material volume) the lifespan of a similar quantity of material that resides in the first converters shown and described herein in the presently disclosed systems, apparatuses, and according to the present methods.

According to further present aspects, the present apparatuses, systems, and methods can further incorporate an air management system architecture that directs an airflow through a humidification unit, especially for air supply that is directed to a flight deck. For example, the combined selected positioning of the second ozone converters within the air management system architecture coupled, along with a selected placement of a humidification unit downstream of a second ozone converter can achieve a projected 75% reduction in ozone concentration in an airflow directed to a flight deck.

Further, according to present aspects, a reduction in ozone concentration of about 75% ozone reduction from an airflow directed to and recirculated within a passenger cabin can represent a net ozone concentration reduction system improvement ranging from about 25% to about 30% as compared to ozone concentration reductions achievable in typical aircraft air management systems. Such ozone concentration reduction enhancement, in turn, significantly extends the useful life of the first ozone reducing materials used in first airflow sub-circuit first ozone converter.

In addition, when the second ozone and/or VOC reducing material includes activated carbon, the selected positioning and inclusion of the first airflow sub-circuit second ozone converters comprising the activated carbon can achieve a 75% ozone reduction in the aircraft air management system as described herein, further representing net ozone concentration reduction system improvement ranging from about 25% to about 30% as compared to ozone concentration reductions achievable in typical aircraft air management systems.

According to present aspects, and as used herein, the term "proximate" refers to the relative positioning to one another of two or more components (e.g., in an assembly, etc.) where the two or more components are positioned next to one another and can be in intimate contact with one another in an adjacent orientation. In addition, the term "proximate" is meant to also capture the relative positioning to one another of two or more components where a small gap can occur between the components such that the components may not be in intimate contact across the totality of their adjacent lengths or widths, but are still in close proximity to one another.

When referring to components being in "communication" with one another herein, it is contemplated that the components of the presently disclosed air management systems are configured to direct an airflow through the disclosed systems and apparatuses. Accordingly, with respect to one another to effect an efficient airflow distribution through an object such as, for example, an aircraft, etc., the components are in ducted communication with one another to deliver an airflow through the disclosed systems and apparatuses, and according to the disclosed methods.

Further present aspects are outlined in FIGS. 6, 7, 8, 9, and 10, showing flowcharts that outline methods according to present aspects. As shown in FIG. 6, and according to present aspects, a method 100 for reducing ozone and/or VOC concentration from an aircraft airflow is disclosed, including increasing ozone concentration reduction for existing air purification systems, with the method 100 including providing 102 a first airflow sub-circuit (e.g., in an aircraft air management system, etc., also referred to equivalently as an "air purification system", etc.), with the first airflow sub-circuit configured to deliver a first conditioned airflow to a passenger cabin, and with the first conditioned airflow sub-circuit including at least one first airflow sub-circuit first ozone converter, with the at least one first airflow sub-circuit first ozone converter comprising a first ozone reducing material with the at least one first airflow sub-circuit first ozone converter located upstream of or coincident with at least one air conditioning pack, with the first ozone converter comprising a first ozone reducing material. The first airflow sub-circuit further includes at least one first airflow sub-circuit second ozone converter, the at least one first airflow sub-circuit second ozone converter including at least one of a second ozone and VOC reducing material, with the at least one first airflow sub-circuit second ozone converter located downstream of the at least one air conditioning pack, and with the second ozone converter comprising a second ozone and/or VOC reducing material. The method 100 further includes providing 104 a second airflow sub-circuit in the aircraft air management system, with the second airflow sub-circuit configured to deliver a second conditioned airflow air to a flight deck cabin, with the second airflow sub-circuit configured to exclude entry of conditioned air from the first airflow sub-circuit into the second airflow sub-circuit, with the second airflow sub-circuit including at least one second airflow sub-circuit ozone converter, with the at least one second airflow sub-circuit ozone converter comprising the at least one of the second ozone and the VOC reducing material, and with the at least one second airflow sub-circuit ozone converter located downstream of the at least one air conditioning pack. According to the method 100, the second ozone and/or VOC reducing material is different from the first ozone reducing material. The method 100 can further include excluding 106 entry of the first airflow directed to the passenger cabin air volume from being directed to the flight deck air volume. According to present aspects, the methods outlined in FIG. 6 can incorporate the apparatuses and systems shown in at least one of FIGS. 2, 3 and/or 4, and as described herein.

FIG. 7, is a flowchart outlining further methods according to present aspects, As shown in FIG. 7, a method 200 for reducing ozone and/or VOC concentration from an aircraft is disclosed, including increasing ozone and/or VOC concentration reduction for existing air purification systems, with the method 200 including providing 102 a first airflow sub-circuit (e.g., in an aircraft air management system, etc., also referred to equivalently as an "air purification system", etc.), with the first airflow sub-circuit configured to deliver a first conditioned airflow to a passenger cabin, and with the first conditioned airflow sub-circuit including at least one first airflow sub-circuit first ozone converter, with the at least one first airflow sub-circuit first ozone converter comprising a first ozone reducing material, with the at least one first airflow sub-circuit first ozone converter located upstream of or coincident with at least one air conditioning pack, with the first ozone converter comprising a first ozone reducing material. The first airflow sub-circuit further includes at least one first airflow sub-circuit second ozone converter, the at least one first airflow sub-circuit second ozone converter including a second ozone and/or VOC reducing material, with the at least one first airflow sub-circuit second ozone converter located downstream of the at least one air conditioning pack, and with the second ozone converter comprising a second ozone and/or VOC reducing material. The method 200 further includes providing 104 a second airflow sub-circuit in the aircraft air management system, with the second airflow sub-circuit configured to deliver a second conditioned airflow air to a flight deck cabin, with the second airflow sub-circuit configured to exclude entry of conditioned air from the first airflow sub-circuit into the second airflow sub-circuit, with the second airflow sub-circuit including at least one second airflow sub-circuit ozone converter, with the at least one second airflow sub-circuit ozone converter comprising the second ozone reducing material, and with the at least one second airflow sub-circuit ozone converter located downstream of the at least one air conditioning pack. According to the method, the at least one of the second ozone and the VOC reducing material is different from said first ozone reducing material. The method 200 can further include excluding 106 entry of the first airflow directed to the passenger cabin air volume from being directed to the flight deck air volume. As further shown in FIG. 7, method 200 further includes providing 202 a mix manifold in ducted communication with the first airflow sub-circuit and positioning at least one second ozone converter downstream of the mix manifold. The methods outlined in FIG. 7 can incorporate the apparatuses and systems shown in at least one of FIGS. 2, 3, and/or 4, and as described herein.

FIG. 8, is a flowchart outlining further methods according to present aspects. As shown in FIG. 8, a method 300 for reducing ozone and/or VOC concentration from an aircraft is disclosed, including increasing ozone and/or VOC concentration reduction for existing air purification systems, with the method 200 including providing 102 a first airflow sub-circuit (e.g., in an aircraft air management system, etc., also referred to equivalently as an "air purification system", etc.), with the first airflow sub-circuit configured to deliver a first conditioned airflow to a passenger cabin, and with the first conditioned airflow sub-circuit including at least one first airflow sub-circuit first ozone converter, with the at least one first airflow sub-circuit first ozone converter comprising a first ozone reducing material, with the at least one first airflow sub-circuit first ozone converter located upstream of or coincident with at least one air conditioning pack, with the first ozone converter comprising a first ozone reducing material. The first airflow sub-circuit further includes at least one first airflow sub-circuit second ozone converter, said at least one first airflow sub-circuit second ozone converter including at least one of a second ozone reducing material and a second VOC reducing material, with the at least one first airflow sub-circuit second ozone converter located downstream of the at least one air conditioning pack. The method 300 further includes providing 104 a second airflow sub-circuit in the aircraft air management system, with the second airflow sub-circuit configured to deliver a second conditioned airflow air to a flight deck cabin, with the second airflow sub-circuit configured to exclude entry of conditioned air from the first airflow sub-circuit into said second airflow sub-circuit, with the second airflow sub-circuit including at least one second airflow sub-circuit ozone converter, with the at least one second airflow sub-circuit ozone converter comprising the second ozone reducing material, and with the at least one second airflow sub-circuit ozone converter located downstream of the at least one air conditioning pack. According to the method, the at least one of a second ozone reducing material and a second VOC reducing material is different from said first ozone reducing material. The method 300 can further include excluding 106 entry of the first airflow directed to the passenger cabin air volume from being directed to the flight deck air volume.

As further shown in FIG. 8, method 300 further includes providing 202 a mix manifold in ducted communication with the first airflow sub-circuit, and positioning at least one second ozone converter downstream of the mix manifold, and further includes disposing 302 an auxiliary airflow sub-circuit in communication with the passenger cabin, said auxiliary airflow sub-circuit configured to deliver an auxiliary airflow to a passenger cabin, with the auxiliary airflow sub-circuit including at least one auxiliary recirculation fan configured to direct the auxiliary airflow, with the auxiliary airflow in communication with at least one passenger cabin auxiliary inlet, and wherein the auxiliary airflow sub-circuit is not in ducted communication with the mix manifold. The methods outlined in FIG. 8 can incorporate the apparatuses and systems shown in at least one of FIGS. 2, 3 and/or 4, and as described herein.

FIG. 9 is a flowchart outlining further methods according to present aspects. As shown in FIG. 9, a method 400 for reducing ozone and/or VOC concentration from an aircraft is disclosed, including increasing ozone and/or VOC concentration reduction for existing air purification systems, with the method 200 including providing 102 a first airflow sub-circuit (e.g., in an aircraft air management system, etc., also referred to equivalently as an "air purification system", etc.), with the first airflow sub-circuit configured to deliver a first conditioned airflow to a passenger cabin, and with the first conditioned airflow sub-circuit including at least one first airflow sub-circuit first ozone converter, with the at least one first airflow sub-circuit first ozone converter comprising a first ozone reducing material, with the at least one first airflow sub-circuit first ozone converter located upstream of or coincident with at least one air conditioning pack, with the first ozone converter comprising a first ozone reducing material. The first airflow sub-circuit further includes at least one first airflow sub-circuit second ozone converter, said at least one first airflow sub-circuit second ozone converter including at least one of a second ozone reducing material and a second VOC reducing material, with the at least one first airflow sub-circuit second ozone converter located downstream of the at least one air conditioning pack, and with the second ozone converter comprising the at least one of a second ozone reducing material and a second VOC reducing material. The method 400 further includes providing 104 a second airflow sub-circuit in the aircraft air management system, with the second airflow sub-circuit configured to deliver a second conditioned airflow air to a flight deck cabin, with the second airflow sub-circuit configured to exclude entry of conditioned air from the first airflow sub-circuit into said second airflow sub-circuit, with the second airflow sub-circuit including at least one second airflow sub-circuit ozone converter, with the at least one second airflow sub-circuit ozone converter comprising the at least one of a second ozone reducing material and a second VOC reducing material, and with the at least one second airflow sub-circuit ozone converter located downstream of the at least one air conditioning pack. According to the method, the at least one of a second ozone reducing material and a second VOC reducing material is different from said first ozone reducing material.

The method 400 can further include excluding 106 entry of the first airflow directed to the passenger cabin air volume from being directed to the flight deck air volume. As further shown in FIG. 9, method 400 further includes providing 202 a mix manifold in ducted communication with the first airflow sub-circuit, and positioning at least one second ozone converter downstream of the mix manifold, and further includes disposing 302 an auxiliary airflow sub-circuit in communication with the passenger cabin, said auxiliary airflow sub-circuit configured to deliver an auxiliary airflow to a passenger cabin, with the auxiliary airflow sub-circuit including at least one auxiliary recirculation fan configured to direct the auxiliary airflow, with the auxiliary airflow in communication with at least one passenger cabin auxiliary inlet, and wherein the auxiliary airflow sub-circuit is not in ducted communication with the mix manifold.

In another aspect, as shown in FIG. 9, method 400 further includes disposing 402 at least one second airflow sub-circuit ozone converter proximate to and downstream of the at least one auxiliary recirculation fan. In an alternate aspect, the at least one second airflow sub-circuit ozone converter proximate to and upstream the at least one auxiliary recirculation fan. The methods outlined in FIG. 9 can incorporate the apparatuses and systems shown in at least one of FIGS. 2, 3, and/or 4, and as described herein.

In another aspect, shown in FIG. 10, according to a present aspect, a further method is disclosed, with the method 500 including modifying 502 an existing aircraft air management system (referred to equivalently herein as "an aircraft air purification system") to decrease ozone and/or VOC concentration in an aircraft interior with the existing aircraft management system including a first airflow sub-circuit configured to condition air for delivery into a passenger cabin air volume, with the first airflow sub-circuit comprising at least one first airflow sub-circuit first ozone converter, and with the at least one first airflow sub-circuit first ozone converter containing a first ozone reducing material, a mix manifold and at least one air conditioning pack positioned upstream of the mix manifold. The method 500 further includes introducing 504 at least one second ozone converter to the first airflow sub-circuit, with the at least one second ozone converter containing at least one of a second ozone reducing material and a second VOC reducing material, and introducing a second airflow sub-circuit to the existing air management system, with the second airflow sub-circuit configured to deliver an air supply into a flight deck air volume, with the second airflow sub-circuit comprising at least one second airflow sub-circuit second ozone converter consisting of the at least one of a second ozone reducing material and a second VOC reducing material. The method 500 further includes, introducing and/or positioning 506 the second airflow sub-circuit second ozone converter positioned in communication with and proximate to a flight deck air volume inlet. Method 500 further includes positioning 508 the at least one first airflow sub-circuit first ozone converter upstream of or coincident with the at least one air-conditioning pack, and positioning 510 the at least one first airflow sub-circuit second ozone converter downstream of the at least one air-conditioning pack, with the first ozone reducing material differing from the at least one of a second ozone reducing material and a second VOC reducing material. The methods outlined in FIG. 10 can incorporate the apparatuses and systems shown in at least one of FIGS. 2, 3 and/or 4, and as described herein.

The present aspects may, of course, be carried out in other ways than those specifically set forth herein without departing from essential characteristics of the present disclosure. The present aspects are to be considered in all respects as illustrative and not restrictive, and all changes coming within the meaning and equivalency range of the appended claims are intended to be embraced therein.

What is claimed is:

1. An air purification system comprising:
   at least one air conditioning pack;
   a first airflow sub-circuit configured to deliver a first conditioned airflow to a passenger cabin air volume, said first conditioned airflow in communication with the at least one air conditioning pack, said first airflow sub-circuit comprising:
      at least one first airflow sub-circuit first ozone converter, said at least one first airflow sub-circuit first ozone converter comprising a first ozone reducing material, said at least one first airflow sub-circuit first ozone converter located upstream of or located coincident with the at least one air conditioning pack;
      at least one first airflow sub-circuit second ozone converter, said
      at least one first airflow sub-circuit second ozone converter comprising at least one of a second ozone reducing material and a second VOC reducing material, said at least one first airflow sub-circuit second ozone converter located downstream of the at least one air conditioning pack;
   a second airflow sub-circuit configured to deliver a second conditioned airflow air to a flight deck air volume, said second airflow sub-circuit configured to exclude entry of conditioned air from the first airflow sub-circuit into said second airflow sub-circuit, said second airflow sub-circuit comprising:
      at least one second airflow sub-circuit ozone converter, said at least one second airflow sub-circuit ozone converter comprising the at least one of the second ozone reducing material and the second VOC reducing material, said at least one second airflow sub-circuit ozone converter located downstream of the at least one air conditioning pack;
   wherein the air purification system further comprises a mix manifold downstream of and in communication with the at least one air conditioning pack, and at least one recirculation fan in communication with a mix manifold;
   wherein the at least one first airflow sub-circuit further comprises a plurality of passenger cabin airflow inlets, said plurality of passenger cabin airflow inlets located downstream of the mix manifold;
   wherein the first ozone converting material differs from the at least one of the second ozone reducing material and the second VOC reducing material;
   wherein the at least one first airflow sub-circuit second ozone converter is located proximate to at least one of the plurality of passenger cabin airflow inlets; and
   wherein the first airflow sub-circuit further comprises at least one first airflow sub-circuit second ozone converter located proximate to and downstream of at least one auxiliary recirculation fan.

2. The air purification system of claim 1, wherein the at least one first airflow sub-circuit second ozone converter is located at each of the plurality of passenger cabin airflow inlets.

3. The air purification system of claim 1, wherein the first airflow sub-circuit further comprises a first airflow sub-circuit second ozone converter located proximate to and downstream of the at least one auxiliary recirculation fan, said at least one auxiliary recirculation fan configured to direct an auxiliary airflow, said auxiliary airflow in communication with at least one passenger cabin auxiliary inlet, said auxiliary airflow not in ducted communication with the mix manifold.

4. The apparatus of claim 1, wherein at least one of the second airflow sub-circuit and the first airflow sub-circuit further comprises at least one second airflow sub-circuit ozone converter located proximate to and downstream from the at least one air conditioning pack and upstream from the mix manifold.

5. An aircraft comprising the air purification system of claim 1.

6. An aircraft comprising the air purification system of claim 3.

7. An aircraft comprising the air purification system of claim 4.

8. A method comprising:
   providing a first airflow sub-circuit in an aircraft air management system, said first airflow sub-circuit configured to deliver a first conditioned airflow to a passenger cabin, said first conditioned airflow sub-circuit comprising:
      at least one first airflow sub-circuit first ozone converter, said at least one first airflow sub-circuit first ozone converter comprising a first ozone reducing material, said at least one first airflow sub-circuit first ozone converter located upstream of or coincident with at least one air conditioning pack;

at least one first airflow sub-circuit second ozone converter, said at least one first airflow sub-circuit second ozone converter comprising at least one of a second ozone reducing material and a second VOC reducing material, said at least one first airflow sub-circuit second ozone converter located downstream of the at least one air conditioning pack;

providing a second airflow sub-circuit in the aircraft air management system, said second airflow sub-circuit configured to deliver a second conditioned airflow air to a flight deck cabin, said second airflow sub-circuit configured to exclude entry of conditioned air from the first airflow sub-circuit into said second airflow sub-circuit, said second airflow sub-circuit comprising:

at least one second airflow sub-circuit ozone converter, said at least one second airflow sub-circuit ozone converter comprising the at least one of the second ozone reducing material and the second VOC reducing material, said at least one second airflow sub-circuit ozone converter located downstream of the at least one air conditioning pack;

disposing an auxiliary airflow sub-circuit in communication with the passenger cabin, said auxiliary airflow sub-circuit configured to deliver an auxiliary airflow to a passenger cabin, said auxiliary airflow sub-circuit comprising at least one auxiliary recirculation fan configured to direct the auxiliary airflow, said auxiliary airflow in communication with at least one passenger cabin auxiliary inlet;

disposing said at least one second airflow sub-circuit ozone converter proximate to and downstream of the at least one auxiliary recirculation fan;

wherein said auxiliary airflow sub-circuit is not in ducted communication with a mix manifold; and wherein said at least one of the second ozone reducing material and the second VOC reducing material is different from said first ozone reducing material.

9. A method comprising:

providing a first airflow sub-circuit in an aircraft air management system, said first airflow sub-circuit configured to deliver a first conditioned airflow to a passenger cabin, said first conditioned airflow sub-circuit comprising:

at least one first airflow sub-circuit first ozone converter, said at least one first airflow sub-circuit first ozone converter comprising a first ozone reducing material, said at least one first airflow sub-circuit first ozone converter located upstream of or coincident with at least one air conditioning pack;

at least one first airflow sub-circuit second ozone converter, said at least one first airflow sub-circuit second ozone converter comprising at least one of a second ozone reducing material and a second VOC reducing material, said at least one first airflow sub-circuit second ozone converter located downstream of the at least one air conditioning pack;

providing a second airflow sub-circuit in the aircraft air management system, said second airflow sub-circuit configured to deliver a second conditioned airflow air to a flight deck cabin, said second airflow sub-circuit configured to exclude entry of conditioned air from the first airflow sub-circuit into said second airflow sub-circuit, said second airflow sub-circuit comprising:

at least one second airflow sub-circuit ozone converter, said at least one second airflow sub-circuit ozone converter comprising the at least one of the second ozone reducing material and the second VOC reducing material, said at least one second airflow sub-circuit ozone converter located downstream of the at least one air conditioning pack;

disposing an auxiliary airflow sub-circuit in communication with the passenger cabin, said auxiliary airflow sub-circuit configured to deliver an auxiliary airflow to a passenger cabin, said auxiliary airflow sub-circuit comprising at least one auxiliary recirculation fan configured to direct the auxiliary airflow, said auxiliary airflow in communication with at least one passenger cabin auxiliary inlet;

disposing said at least one second airflow sub-circuit ozone converter proximate to and downstream of the at least one auxiliary recirculation fan;

providing a mix manifold in communication with the first airflow sub-circuit;

positioning at least one second ozone converter downstream of the mix manifold;

wherein said at least one of the second ozone reducing material and the second VOC reducing material is different from said first ozone reducing material; and wherein said auxiliary airflow sub-circuit is not in ducted communication with the mix manifold.

* * * * *